(12) United States Patent
Brown et al.

(10) Patent No.: US 11,759,583 B2
(45) Date of Patent: *Sep. 19, 2023

(54) SYSTEMS AND METHODS FOR REDUCING CONTAMINANTS IN A PORTION OF A PATIENT

(71) Applicant: Clyra Medical Technologies, Inc., Westminster, CA (US)

(72) Inventors: Spencer Brown, Westminster, CA (US); Brock Liden, Westminster, CA (US); Tanya Rhodes, Westminster, CA (US); Joe Almasy, Westminster, CA (US); Steven V. Harrison, Westminster, CA (US); Douglas J. Morgan, Westminster, CA (US)

(73) Assignee: Clyra Medical Technologies, Inc., Westminster, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/461,544

(22) Filed: Aug. 30, 2021

(65) Prior Publication Data
US 2021/0386942 A1 Dec. 16, 2021

Related U.S. Application Data

(63) Continuation of application No. 16/714,288, filed on Dec. 13, 2019, now Pat. No. 11,103,657.
(Continued)

(51) Int. Cl.
*A61M 13/00* (2006.01)
*A61B 1/317* (2006.01)
(Continued)

(52) U.S. Cl.
CPC .......... *A61M 13/003* (2013.01); *A61B 1/015* (2013.01); *A61B 1/018* (2013.01); *A61B 1/04* (2013.01);
(Continued)

(58) Field of Classification Search
CPC .......... A61B 1/015; A61B 1/018; A61B 1/04; A61B 1/043; A61B 1/317;
(Continued)

(56) References Cited

U.S. PATENT DOCUMENTS

| 5,382,229 | A | 1/1995 | Grabenkort et al. | |
| 6,569,839 | B1 * | 5/2003 | McKay | A61M 1/77 |
| | | | | 514/59 |

(Continued)

FOREIGN PATENT DOCUMENTS

WO WO 2009/045478 A1 4/2009

*Primary Examiner* — Anh Tuan T Nguyen
*Assistant Examiner* — Shankar Raj Ghimire
(74) *Attorney, Agent, or Firm* — STERNE, KESSLER, GOLDSTEIN & FOX P.L.L.C.

(57) ABSTRACT

Systems and methods for reducing pathogens near an implant are discussed. In some cases, the methods include reducing contaminants in a portion of a patient that has an implant and that is disposed interior to a closed surface of skin of the patient. The method can further include placing a conduit in the closed surface of skin and flowing an antimicrobial fluid into that portion of the patient to contact the antimicrobial fluid with a surface of the implant and tissue adjacent to the implant. In some cases, the antimicrobial fluid is then removed from the portion of the patient having the implant. As part of this method, biofilm near the implant can be mechanically, ultrasonically, electrically, chemically, enzymatically, or otherwise disrupted. Other implementations are described.

5 Claims, 7 Drawing Sheets

Related U.S. Application Data

(60) Provisional application No. 62/779,405, filed on Dec. 13, 2018.

(51) Int. Cl.
*A61M 1/00* (2006.01)
*A61B 90/00* (2016.01)
*A61B 1/018* (2006.01)
*A61B 1/015* (2006.01)
*A61B 1/04* (2006.01)
*A61B 17/00* (2006.01)

(52) U.S. Cl.
CPC ............... *A61B 1/317* (2013.01); *A61M 1/77* (2021.05); *A61M 13/00* (2013.01); *A61M 13/006* (2014.02); *A61B 2017/0034* (2013.01); *A61B 2090/3912* (2016.02); *A61B 2090/3933* (2016.02); *A61B 2090/3941* (2016.02); *A61M 1/85* (2021.05); *A61M 2205/0205* (2013.01)

(58) Field of Classification Search
CPC .... A61B 2017/0034; A61B 2090/3912; A61B 2090/3933; A61L 2/025; A61M 1/0058; A61M 1/77; A61M 13/00; A61M 13/003; A61M 2205/0205; A61M 2205/3334; A61M 3/0283
See application file for complete search history.

(56) References Cited

U.S. PATENT DOCUMENTS

| | | |
|---|---|---|
| 6,916,296 B2 | 7/2005 | Soring et al. |
| 7,942,864 B2 | 5/2011 | Hynes |
| 9,623,178 B2 | 4/2017 | Krebs et al. |
| 9,943,639 B2 | 4/2018 | Germain et al. |
| 10,178,942 B2 | 1/2019 | Germain et al. |
| 2005/0038378 A1* | 2/2005 | Lastovich ......... A61M 5/14244 604/47 |
| 2006/0224103 A1* | 10/2006 | Rontal ................... A61B 17/24 604/22 |
| 2006/0268393 A1 | 11/2006 | Islam |
| 2007/0239078 A1 | 10/2007 | Jaeb |
| 2008/0249483 A1 | 10/2008 | Slenker et al. |
| 2009/0054881 A1 | 2/2009 | Krespi |
| 2009/0093713 A1 | 4/2009 | Hyde et al. |
| 2009/0264809 A1 | 10/2009 | Sen |
| 2010/0256607 A1 | 10/2010 | Burnett |
| 2011/0112408 A1 | 5/2011 | Greenstein et al. |
| 2012/0253125 A1 | 10/2012 | Slenker et al. |
| 2013/0035561 A1 | 2/2013 | Sharkey et al. |
| 2014/0194810 A1 | 7/2014 | Barsoum et al. |
| 2017/0112577 A1* | 4/2017 | Bonutti ............... G06T 7/11 |
| 2018/0206704 A1* | 7/2018 | Spector ............. A61B 10/0283 |
| 2018/0353338 A1 | 12/2018 | Locke et al. |
| 2018/0353341 A1* | 12/2018 | Locke ............... A61F 13/15203 |
| 2019/0069831 A1 | 3/2019 | Kuck et al. |
| 2019/0159663 A1* | 5/2019 | Krstajic ............... A61B 5/0071 |

* cited by examiner

SYSTEMS AND METHODS FOR REDUCING CONTAMINANTS IN A PORTION OF A PATIENT

CROSS-REFERENCE TO RELATED APPLICATION

This application claims priority to U.S. Nonprovisional Application No. 16/714,288, which was filed on Dec. 13, 2019, which application claims priority to U.S. Provisional Application No. 62/779,405, which was filed on Dec. 13, 2018, and which is entitled SYSTEMS AND METHODS FOR REDUCING CONTAMINANTS IN A PORTION OF A PATIENT, the entire disclosure of which is hereby incorporated herein.

BACKGROUND OF THE INVENTION

Field of the Invention

The present invention relates to systems and methods for reducing pathogens, infections, and/or other contaminants in a portion of a patient. More particularly, some implementations of the described invention relate to systems and methods for reducing contaminants in a portion of a patient that has an implant and that is disposed interior to a closed surface of skin of the patient. The method can further include placing one or more relatively small openings into the closed surface of skin and injecting, pulsing, introducing, and/or otherwise flowing an antimicrobial material into that portion of the patient to contact the antimicrobial material with a surface of the implant and/or tissue adjacent to the implant. In some cases, the antimicrobial material flows into the portion of the patient faster than it flows out, such that differential pressure between inflow and outflow of the antimicrobial material causes that portion of the patient to inflate. In some cases, once inflated, the rate of inflow and outflow are maintained at a similar level so as to continue to flush (while maintaining inflation of) the portion of the patient. In some cases, after treatment with the antimicrobial material, it is then flushed, drained, suctioned out, or otherwise removed from the portion of the patient having the implant. As part of this method, biofilm and/or other contaminants near the implant are, in some implementations, disrupted mechanically, ultrasonically, electrically, chemically, enzymatically, and/or in any other suitable manner. Thus, in some implementations, the described systems and methods can treat infections and/or other contaminants near implants in a relatively non-invasive manner.

Background and Related Art

People receive implants in their bodies for a wide variety of reasons. In some cases, people get implants for cosmetic reasons in an effort to improve or otherwise change their appearance. In some other cases, however, people get implants to replace or support a worn or damaged joint or bone. In this regard, when a person's joint or bone is worn or damaged, such person's mobility and lifestyle can be dramatically and negatively impacted. In contrast, when an implant is placed in such person to replace or strengthen that person's damaged joint or bone, that person's life can be greatly improved. Indeed, in many such cases, an implant can readily help a person by improving mobility, reducing pain, and (often times) greatly improving such person's lifestyle.

In some rare instances, however, when a person gets an implant (or sometime thereafter), tissue (or another portion of the person's body) that is near the implant can become infected. In some cases, such an infection can make that person become sick, can cause swelling around the implant, can (if not effectively treated) require amputation, and (in some cases) can even result in death.

Such infections can be treated in a variety of manners. Indeed, for some infections that are relatively easy to treat, antibiotics are taken orally. In some more difficult cases, however, an implant in an infected area of a patient must be removed and/or replaced. In some such cases, the person's body is reopened through one or more relatively large incisions, such that the implant is exposed. Moreover, as the old implant is removed, the surrounding tissue is often extensively debrided. In some cases, scar tissue is also debulked, soft tissue is released, and/or an osteotomy is performed. In other words, many such procedures can be relatively invasive.

Where an implant is replaced, such a replacement can take place in a variety of manners, including through a one-step re-implantation procedure or a two-step re-implantation procedure. Generally, in the one-step re-implantation procedure, the old implant is removed and a new implant is installed during a single surgery. As such a procedure is typically somewhat less successful at removing infection than is the two-step procedure, this one-step procedure is not as popular in the United States as is the two-step procedure. In fact, the one-step procedure is (in the United States) often reserved for people who are considered too sick or too weak to undergo the prolonged two-step procedure.

With respect to the two-stage re-implantation procedure, this procedure typically involves performing a first surgery in which the old implant is removed and in which an antibiotic cement spacer is placed in the place of the old implant (e.g., between the tibia and femur) to preserve a desired space or gap between bones. In some cases, the incisions from the first surgery in the two-part procedure are then closed, and the person is then required to wait (with reduced mobility) for an extended period of time (often, multiple weeks) for the antibiotic to stop the infection. In some cases, after the long wait, a second surgery is performed, the cement spacer is removed, and a new implant is inserted.

In any case, whether an infection near an implant is treated through a one-step or a two-step re-implantation procedure, such treatments can have many shortcomings. Indeed, in some cases in which a person is cut open to expose an implant for removal and/or replacement, the person can now have another major wound that needs to heal. This healing process can, in some cases, be even longer and more extensive, with increased scarring, where the implant is replaced. Moreover, in many cases, implant replacement procedures can involve: relatively longer periods of hospitalization, relatively longer amounts of physical therapy, a significant amount of pain and discomfort, loss of range of motion, relatively high risks of reinfection, extensive costs and fees (e.g., in operating room fees, hospital fees, antibiotics, loss of work, physician fees, physical therapy fees, replacement implant costs, etc.), and otherwise include a number of undesirable side effects.

Thus, while systems and methods currently exist that are used to treat infections near implants, some challenges still exist, including those listed above. Accordingly, it would be an improvement in the art to augment or even replace current techniques with other techniques.

SUMMARY OF THE INVENTION

The present invention relates to systems and methods for reducing pathogens, infections, and/or other contaminants in a portion of a patient. More particularly, some implementations of the described invention relate to systems and methods for reducing contaminants in a portion of a patient that has an implant and that is disposed interior to a closed surface of skin of the patient. The method can further include placing one or more relatively small openings into the closed surface of skin and injecting, pulsing, introducing, and/or otherwise flowing an antimicrobial material into that portion of the patient to contact the antimicrobial material with a surface of the implant and/or tissue adjacent to the implant. In some cases, the antimicrobial material flows into the portion of the patient faster than it flows out, such that differential pressure between inflow and outflow of the antimicrobial material causes that portion of the patient to inflate. In some cases, once inflated, the rate of inflow and outflow are maintained at a similar level so as to continue to flush (while maintaining inflation of) the portion of the patient. In some cases, after treatment with the antimicrobial material, it is then flushed, drained, suctioned out, or otherwise removed from the portion of the patient having the implant. As part of this method, biofilm and/or other contaminants near the implant are, in some implementations, disrupted mechanically, ultrasonically, electrically, chemically, enzymatically, and/or in any other suitable manner. Thus, in some implementations, the described systems and methods can treat infections and/or other contaminants near implants in a relatively non-invasive manner.

In some implementations, the described systems and methods involve having a practitioner identify an infection and/or other form of contamination (or potential contamination) in a patient. In some cases, such contamination is not localized near an implant. In some other cases, however, the contamination is localized near an implant (e.g., a joint replacement, a cosmetic implant, a pacemaker, a plate, a bolt, a dental implant, a mesh implant, and/or any other implant).

Unlike some conventional methods for treating infections near implants, which involve cutting open the patient to substantially expose the implant (e.g., to wash and/or replace the implant), some implementations of the described systems and methods involve leaving the implant in the patient and placing one or more relatively small openings in a closed portion of the patient's skin (e.g., near the implant). In some such cases, one or more openings in the patient and near the implant each act as both an inlet and an outlet for an antimicrobial and/or any other material or object that is placed into an internal space of the patient near the implant. In some other embodiments, however, one or more openings function as inlets to allow one or more antimicrobials, contaminant disruption chemicals, rinsing agents, tools, abrasive materials, "low frequency" ultrasound transducers, ultrasound transducers, vibrating brushes, electrodes, cameras, microfluidics, and/or other materials or objects to be introduced into an internal space of the patient (e.g., a space in the patient that is near the implant and that, in some cases, becomes enlarged or inflated as such materials are introduced into the patient).

Additionally, in some embodiments, one or more openings in the closed portion of the patient's skin function as outlets to allow the antimicrobials, contaminant disruption chemicals, rinsing agents, tools, abrasive materials, and/or other materials or objects to be flushed from and/or to otherwise exit the internal space in the patient. Thus, in some embodiments, antimicrobials and/or other materials can flow into and out of the patient (e.g., through a portion of the patient that is substantially closed with the exception of one or more relatively small openings formed therein).

Where the antimicrobials and/or other materials are injected, pulsed, introduced, and/or otherwise caused or allowed to flow into and/or out of a patient (e.g., a closed portion of the patient), such materials can flow through the patient, be held in, dwell within a pressurized capsular area, and/or otherwise be introduced into the patient in any suitable manner. Some examples of suitable methods for flowing such materials into and/or through the patient include, but are not limited to, having such materials be gravity fed into the patient, having such materials be pulsed (or pulsated) into the patient, having such materials inflate a portion of the patient, sucking such materials into and/or out of the patient, pressurizing such materials within the patient, injecting such materials into the patient through one or more of the openings, having such materials have a hydrostatic flow into and/or through the internal space of the patient, having such materials have a hydraulic flow into and/or through the internal space, having such materials have a laminar flow into and/or through the internal space, having such materials have a turbulent flow into and/or through the internal space, flowing such materials through a pulsed lavage technique into and/or through the internal space, flowing such materials into and/or through the internal space using a lavage technique, having such materials have any suitable dwell time within the internal space in the patient, having such materials serve as a medium for a ultrasound and/or sonic producing device (e.g., an ultrasonic vibrator) while such materials are entering, dwelling within, and/or exiting the internal space, having such materials serve as a medium for carrying an electrical current (e.g., before and/or when such materials pass through the patient), having such materials be jetted into and/or through the internal space, having such materials be warmed and/or heated (e.g., in any suitable manner, including, without limitation, via electrolysis, being exposed to heat from a heating element, and/or in any other suitable manner) before or while in the patient, having such materials be exposed to intermittent pressure and suction (e.g., to expand and contract the internal space, to break up pathogens in the internal space, to drive the antimicrobial and/or other materials into and out of crevices in the internal space, and/or for any other suitable purpose), and/or in any other suitable manner. Indeed, in some implementations, such methods include heating such materials before and/or while in the patient (e.g., via a heater and/or in any other suitable, whether disposed outside and/or inside the internal space) to any suitable temperature (including, without limitation, heating such materials to about 37° degrees C.±3° C.) and/or in such a manner so as to increase the antimicrobial activity and/or healing characteristics of such materials.

Additionally, in some implementations, one or more materials (e.g., an antimicrobial, a saline solution, and/or any other suitable fluid) are injected or otherwise introduced into an internal space of the patient under pressure such that the internal space inflates and the materials are able to fill and be infused throughout the internal space. In some such implementations, the materials are then allowed to remain or dwell in the internal space of the patient for any suitable amount of time (e.g., for between 0 seconds and about 8 hours, or within any subrange thereof, such as for between about 10 seconds and about 2 hours). Moreover, in some such embodiments, some or all of the materials are sucked out (e.g., via a negative pressure device, a tool comprising a vacuum port, a vacuum, and/or in any other suitable manner), pressed out, flushed, allowed to drain, and/or otherwise removed from the internal space in the patient.

Furthermore, in some such cases, the process of flowing one or more materials into the internal space and then removing such materials from the internal space is repeated any suitable number of times. Indeed, in some cases, one or more materials are forced (or otherwise flow) into the internal space under pressure, with such materials being allowed to stay in the inflated internal space for a desired period of time, and then some or all of the materials are flushed, drained, and/or otherwise removed from the internal space. Although in some such cases, one type of material (e.g., an antimicrobial) is forced into and removed from the internal space multiple times, in some other cases, two or more different types of materials (e.g., antimicrobials, rinsing fluids, and/or any other suitable materials) are flowed into and out of the internal space, either together or at separate times. Additionally, although this process, whether repeated or not, can take place over any suitable period of time, in some implementations, it is accomplished during the duration of a single surgery (e.g., a single surgical procedure) on the patient.

Also, in some implementations, when the materials are introduced into the internal space at multiple different times they are introduced each time into the internal space at about the same pressure. In some other implementations, however, such materials are introduced into the internal space at different pressures. Indeed, in some embodiments, the first time a fluid is introduced into the internal space, the fluid is caused to inflate the internal space (e.g., a synovial joint) to a first pressure (or such that the internal space receives a first amount of fluid). In some such embodiments, the second time a fluid is introduced into the internal space, such fluid (whether it be the same as the fluid used the first time or different) is caused to inflate the internal space to a different pressure (e.g., either a higher or a lower pressure) and/or more fluid is introduced into the internal space than was present the first time. For instance, the second time, the internal pressure of the internal space is caused to be higher or more fluid is introduced—thus causing the internal space to iteratively grow larger between the first time and the second time (and/or any other suitable time) that fluid is introduced into the internal space. In such a manner, some implementations of the described systems and methods can help expose and/or remove contaminants within a patient, while reducing and/or preventing unnecessary tearing, pain, and/or discomfort.

In some other implementations, the antimicrobial (and/or any other suitable fluid) is caused to flow more rapidly into the internal space that is being treated than such antimicrobial (and/or other fluid) flows out of that space. As a result of this differential flow, in some cases, the antimicrobial (and/or other fluid) causes that portion of the patient to expand or to otherwise inflate with the antimicrobial (and/or other fluid). As the antimicrobial (or other fluid) is able to flow through the inflated portion of the patient, the antimicrobial is able to spread throughout, expand, leak into, and penetrate into various portions of that portion of the patient (e.g., ensuring that the antimicrobial contacts contaminants that may otherwise be inaccessible to the antimicrobial). Additionally, in some cases, this differential flow causes the antimicrobial to churn, swirl, and/or to otherwise mix (e.g., with contaminants) within such internal space. Accordingly, in some cases, this differential flow helps to churn up contaminants and to ensure that they are exposed to the antimicrobial.

Where the antimicrobial and/or other fluid flows into the portion of the patient that comprises an implant faster than such fluid flows out, the flow differential can be created in any suitable manner. Indeed, in some cases, the portion of the patient being treated comprises: fewer outlets than inlets, one or more inlets having a larger inner diameter than does the fluid outlet(s), one or more fluid outlets (e.g., outlet conduits) that are valved (e.g., with a variable valve) to control fluid outflow; one or more inlets that are valved (e.g., to allow for increased inflow); and/or any other suitable feature that allows fluid to flow into that portion of the patient faster than it exits (at least for some portion of the time that such fluid is flowed into that portion of the patient).

In some cases, once the portion of the patient has been inflated (e.g., with the antimicrobial and/or any other suitable fluid), the rate of inflow to and outflow from that portion of the patient are maintained at similar levels so as to continue to flush (while maintaining inflation of) that portion of the patient. In this regard, such inflow and/or outflow rates can be modified in any suitable manner that allows the method function as just described. For instance, one or more valves, pumps, flow limiters, actuators, vacuums, and/or other aspects of the described systems and methods can be slowed, sped up, stopped, started, and/or otherwise be modified (e.g., automatically and/or manually) to obtain a flow equilibrium that keeps the portion of the patient inflated for a desired period of time.

To help the antimicrobial (and/or any other suitable fluid) penetrate and spread throughout a portion of a patient that comprises an implant, in some cases, once the antimicrobial and/or other fluid is introduced into that portion of the patient, that portion of the patient is moved through a range of motion, bent, worked, massaged, rubbed, vibrated (e.g., with a vibrating mechanism that is disposed outside and/or inside the internal space), and/or otherwise manipulated. Indeed, in some cases in which the portion of the patient that is being treated is a joint (e.g., a knee, hip, etc.), that joint is moved through a range of motion to help the antimicrobial to flow throughout the joint to help reduce contaminants that would likely have received little to no (or at least not a desired amount of) exposure to the antimicrobial without such manipulation.

In some cases, the described systems and methods optionally involve loosening, dissolving, breaking up, killing, stopping, or slowing the growth of, sterilizing, removing, fracturing, and/or otherwise disrupting biofilm and/or other contaminants in the patient (e.g., at or near an implant). In this regard, such contamination disruption can be performed in any suitable manner, including, without limitation, through ultrasound (e.g., at any suitable frequency, including, without limitation, between about 20 kHz and about 1 MHz, or within any subrange thereof), low frequency ultrasound (including, without limitation, between about 20 kHz and 80 kHz, or within any subrange thereof), and/or other sonic vibrations or excitement; by mechanically contacting the contaminants (e.g., with a brush, deburring device, vibrating brush, vibrating contact material, scraper, material that is abrasive to contaminants, debriding device, and/or any other suitable device that is capable of contacting contaminants within an internal space of the patient through one or more of the openings); by applying an electrical field to the contaminants, the antimicrobial, the influent, and/or any other portion of the internal space and/or materials that flow therein (e.g., prior to and/or after introduction into the internal space); by applying electrostatic forces to the contaminants; by applying Van der Walls forces to the contaminants; by applying magnetic fields to the contaminants; by contacting the contaminants with electrolyzed materials; by electrolyzing the contaminants; by introducing electrically charged fluid into contact with the contaminants; by providing electrical stimulation to the contaminants and/or other materials in the internal space (e.g., pulsed and/or any other suitable type of electrical stimulation); by applying one or more contaminant disruption chemicals (e.g., one or more acids, bases, surfactants, emulsifiers, enzymes, antimicrobials, and/or any other chemical or chemicals that are capable of disrupting contaminants in the patient) to the contaminants; by applying an abrasive material to such contaminants; by flowing one or more fluids through the patient under pressure; by exciting a fluid within the internal space by flowing such fluid with a varied pressure (e.g., pulsed lavage and/or any other suitable pressure variation technique); by applying suction (e.g., intermittent or any other suitable type of suction) to fluids and/or contaminants in the internal space; by inflating and deflating the internal space (e.g., one or more times); by flowing a fluid past the contaminants with a hydrostatic and/or hydraulic flow; by flowing a fluid past the contaminants with a laminar flow; by flowing a fluid past the contaminants with a turbulent flow; by jetting a fluid past contaminants (e.g., via lavage, pulsed lavage, and/or in any other suitable manner); by applying heat to an exterior surface of the internal space; and/or by otherwise disrupting such contaminants in any suitable manner.

Indeed, in one example, one or more contaminant disruption chemicals (e.g., acetic acid) are introduced into the patient through one or more of the openings (e.g., near the implant). In another example, ultrasonic vibrations are applied to a fluid within the internal space (e.g., as the fluid flows into, dwells within, and/or exits the internal space) to help disrupt contaminants.

Although one or more of the various materials that are placed in the patient through the openings (e.g., an antimicrobial material) can be left in the patient indefinitely, in some other cases, one or more of such materials (e.g., one or more antimicrobial materials, contaminant disruption chemicals, saline solutions, amounts of water, debrisan beads, abrasive materials, and/or any other such materials) are introduced into and then are flushed or otherwise removed from the patient (e.g., from the internal space around the implant). In this regard, such materials can be flushed or otherwise removed from the internal space in the patient in any suitable manner, including, without limitation, through: irrigation, using a fluid (e.g., water, saline, gel, and/or any other suitable fluid) to flush the materials from the patient, aspiration, a negative pressure wound therapy device, a suction device, a vacuum, the application of pressure to an outer surface of the patient to force the materials towards one or more of the openings, gravity, allowing the internal space to drain, and/or in any other suitable manner.

Indeed, in some embodiments, while (and/or after) one or more materials (e.g., contaminant disruption chemicals, antimicrobials, abrasive materials, etc.) are introduced into the patient through one or more of the openings, such materials (along with any contaminants and/or biomaterials that are washed out with such materials) are extracted or otherwise removed through one or more of the openings in the patient through the use of one or more negative pressure wound therapy devices. Indeed, in some implementations (as discussed above) some such materials are used to enlarge and/or otherwise inflate an internal space and are then sucked and/or otherwise removed from the internal space one or more times (e.g., new material is moved through and/or used material is recirculated through (for instance, after being filtered) the internal space).

The described systems and methods can be varied in any suitable manner. Indeed, any portion of the described methods can be modified, omitted, repeated, replaced, augmented, performed in series, performed in parallel, reordered, and/or otherwise be changed in any suitable manner that allows contaminants in a patient to be reduced. By way of example, some implementations of the described methods comprise forming one or more openings in the patient (e.g., near an implant) and flowing one or more antimicrobials into and/or through the patient so as to contact the antimicrobials with a surface of an implant and/or tissue surrounding the implant. In some such implementations, the antimicrobials are flowed through the patient without any additional contaminant disruption. In some other implementations, one or more forms of contaminant disruption take place before, during, and/or after the antimicrobial is flowed into and/or through the patient.

In some cases, the described systems and methods include inserting one or more cameras (including, without limitation, arthroscopy cameras and/or any other suitable camera) into an internal space of the patient to allow a practitioner to observe the internal space (e.g., placement of inlet and outlet conduits, debridement tool placement, ultrasonic head placement, contamination, and/or other aspects of the internal space). In some cases, however, the described systems and methods include the use of one or more cameras that are capable of detecting the presence and/or quantity of bacteria and/or biofilm in a portion of a patient in real time or near real time. While the systems and methods can include any camera that is capable of functioning in such a manner, in some cases, the camera includes one or more digital cameras, steerable cameras, arthroscopic cameras, infrared cameras, blue light cameras, ultraviolet light illumination cameras having a dual bandpass (and/or any other suitable) optical filter that is configured to detect fluorescence and/or other characteristics of bacteria and/or biofilm, and/or any other suitable camera or sensor that is capable of detecting bacteria in a patient in real time or near real time and that is capable of being at least partially inserted into an internal space in the patient. In some such cases, such a camera allows a practitioner and/or processor to identify bacteria and/or biofilm within the internal space and to then take measures to remove or otherwise reduce such contaminants in the internal space. For instance, in some cases where a practitioner identifies bacteria and/or other contaminants in a certain area within an internal space, the practitioner can apply ultrasonic vibrations to, lavage, flush, and/or otherwise work to break up (e.g., chemically, sonically, and/or mechanically) such bacteria and to remove it from the internal space.

In accordance with some implementations, the described systems and methods relate to one or more implants that comprise one or more antimicrobials. In this regard, the described systems and methods can use any suitable implant, including, without limitation, permanent implants, resorbable implants, orthopedic implants, cosmetic implants, mesh implants, dental implants, shunts, skin implants, bone implants, body tissue implants, ceramic implants, metal implants, plastic implants, stents, ports, screws, bolts, fasteners, couplers, sensors, medicine delivery implants, physical support implants, and/or any other suitable implants that can comprise and/or otherwise be used with one or more antimicrobials.

Additionally, the described antimicrobial that is used in or with an implant can comprise any suitable antimicrobial, including, without limitation, one or more metals, antibiotics, antifungals, biocides, types of iodine, and/or other suitable antimicrobials. Indeed, in some embodiments, silver, gold, copper, and/or any other suitable metal (and/or iodine and/or other suitable material) having antimicrobial characteristics is anodized, vapor deposited, coated, impregnated, infused, and/or otherwise placed on a surface of the implant. In some other embodiments, however, the antimicrobial is impregnated into, disposed in a reservoir within, disposed within a balloon of, used with delayed release polymers, used with delayed resorption polymers, used with any other suitable delayed release and/or resorption systems, and/or otherwise configured to be released slowly from the implant. By way of example, some implants comprise a material that is configured to slowly release an antimicrobial. Some examples of such a material include, without limitation, one or more polymers, lattices, and/or any other suitable materials that are suitable for use in a patient and that are configured to release the antimicrobial over time.

In some implementations, the implant comprising one or more antimicrobials comprises one or more resorbable materials that are configured to be resorbed into the patient. Some examples of such materials include, but are not limited to, calcium phosphate, calcium sulfate, gelatin, hydrofibers, carrageenan, resorbable glass, resorbable ceramic, poly(methyl methacrylate), and/or any other suitable material that can comprise an antimicrobial and be resorbed into the patient. Accordingly, in some cases, a resorbable implant (e.g., one or more beads, pins, bolts, screws, plates, gels, powders, and/or other suitable implants) with one or more antimicrobials can be implanted into a person, where the implant can act as an antimicrobial device for an extended period of time (e.g., until it is resorbed). In accordance with some embodiments, the described systems and methods include a system that is configured to provide one or more antimicrobials (and/or any other suitable materials) into a patient and to receive such antimicrobials (and/or any other suitable materials) as they exit the patient. Indeed, some implementations of such a system comprise: a first container that is configured to hold an antimicrobial (and/or any other suitable material) before it is introduced into the patient through one or more of the openings in the patient; a second container that is configured to receive the antimicrobial (and/or any other suitable materials) after it has passed through the patient; one or more conduits to direct the antimicrobial to and/or from an internal space in the patient (e.g., through one or more openings), and/or one or more mechanisms for flowing, sucking (e.g., via a negative pressure wound therapy device, a tool comprising a vacuum port, a vacuum, and/or in any other suitable manner), forcing, and/or otherwise moving the antimicrobial (and/or other materials) through the patient.

Additionally, in some implementations, such a system comprises one or more switches, user interfaces, programs, and/or processors that are configured to allow the system to control one or more aspects of one or more fluids (e.g., a heat, a pressure, a flow pattern, a pulsation, a flow rate, a dwell time within the internal space, ultrasonic vibration, and/or any other suitable characteristic of the fluids) that flow into and/or out of the internal space. Thus, in some implementations, such a system can be automated and/or programmable. Additionally, in some cases, such a system is portable, configured for extended use, and/or is otherwise configured to provide a convenient mechanism for providing the described methods to a patient. Indeed, in some cases, such a system can be coupled to a patient, and the patient can take the system home to receive treatment outside of a care facility. In some other embodiments, however, such a system is configured to reduce contaminants in a patient during a single surgical procedure (e.g., in less than about 8 hours).

While the methods and processes of the present invention may be particularly useful for treating infections near implants, those skilled in the art will appreciate that the described systems and methods can be used in a variety of different applications and in a variety of different areas of manufacture. For instance, some implementations of the described systems and methods are used to treat infections and/or other forms of contamination in patients who do not have an implant or who have an implant but for which the contamination is located in another portion of the patient, away from the implant. In some such implementations, one or more openings can be formed in a closed portion of a patient's skin near a contaminated (or potentially contaminated) site, away from any implant. In such implementations, the described systems and methods can be used to reduce contaminants in the patient at such a site.

These and other features and advantages of the present invention will be set forth or will become more fully apparent in the description that follows and in the appended claims. The features and advantages may be realized and obtained by means of the instruments and combinations particularly pointed out in the appended claims. Furthermore, the features and advantages of the invention may be learned by the practice of the invention or will be obvious from the description, as set forth hereinafter.

BRIEF DESCRIPTION OF THE DRAWINGS

In order that the manner in which the above-recited and other features and advantages of the present invention are obtained, a more particular description of the described inventions will be rendered by reference to specific embodiments thereof, which are illustrated in the appended drawings. Understanding that the drawings are not necessarily drawn to scale or in proper proportion, and that the drawings depict only typical embodiments of the present inventions and are not, therefore, to be considered as limiting the scope of the inventions, the present inventions will be described and explained with additional specificity and detail through the use of the accompanying drawings in which.

DETAILED DESCRIPTION OF EMBODIMENTS OF THE INVENTION

Figure 1:
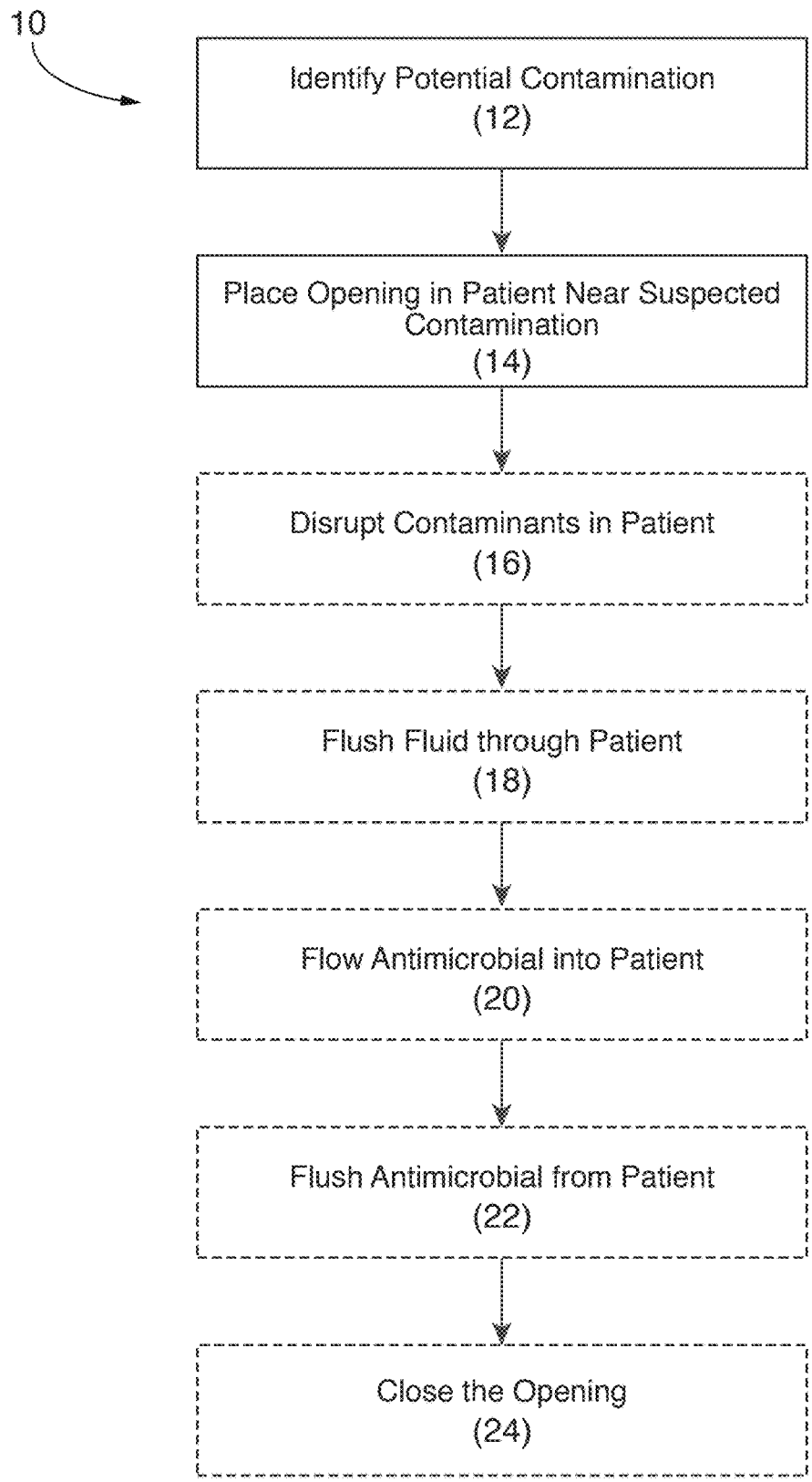
FIG. 1 illustrates a flowchart depicting a method for reducing contaminants in a patient in accordance with a representative embodiment.

The present invention relates to systems and methods for reducing pathogens, infections, and/or other contaminants in a portion of a patient. More particularly, some embodiments of the described invention relate to systems and methods for reducing contaminants in a portion of a patient that has an implant and that is disposed interior to a closed surface of skin of the patient. The method can further include placing one or more relatively small openings into the closed surface of skin and injecting, pulsing, introducing, and/or otherwise flowing an antimicrobial material into that portion of the patient to contact the antimicrobial material with a surface of the implant and/or tissue adjacent to the implant. In some cases, the antimicrobial material flows into the portion of the patient faster than it flows out, such that differential pressure between inflow and outflow of the antimicrobial material causes that portion of the patient to inflate. In some cases, once inflated, the rate of inflow and outflow are maintained at a similar level so as to continue to flush (while maintaining inflation of) the portion of the patient. In some cases, after treatment with the antimicrobial material, it is then flushed, drained, suctioned out, or otherwise removed from the portion of the patient having the implant. As part of this method, biofilm and/or other contaminants near the implant are, in some embodiments, disrupted mechanically, ultrasonically, electrically, chemically, enzymatically, and/or in any other suitable manner. Thus, in some embodiments, the described systems and methods can treat infections and/or other contaminants near implants in a relatively non-invasive manner.

As used herein, the term patient and variations thereof may refer to any person or animal that is capable of receiving an implant and/or being treated with the described systems and methods. In some cases, the term patient refers to a human of any age, including, without limitation, a human who has received an implant.

As used herein, the term practitioner and variations thereof may refer to one or more doctors, nurses, specialists, robots, medical professionals, veterinarians, care providers, and/or anyone or anything else that is or that are capable of performing acts attributed herein to a practitioner.

As used herein, the terms implant, implants, and variations thereof may refer to any suitable material (e.g., bone, skin, metal, ceramic, plastic, polymer, scaffold, lattice, matrix, mesh, tissue, organ, bead, pin, and/or any other suitable material), device, and/or other suitable object that is implanted into a patient. In some cases, the term implants refers to one or more medical devices that are configured to be implanted into a patient. Indeed, in some cases, an implant includes, but is not limited to, one or more orthopedic implants (e.g., hip prostheses, femoral head prostheses, tibial plate prosthesis, intraspinal implants, elbow implants, ankle implants, shoulder implants, and/or any other orthopedic implants), trauma implants, cables, pins, rids, bolts, screws plates, nails, films, sensory and/or neurological implants (e.g., intraocular lens, intrastromal corneal ring segments, cochlear implants, tympanostomy tubes, neurostimulators, and/or other suitable implants), cardio vascular implants (e.g., artificial heart, artificial heart valves, implantable cardioverter-defibrillators, cardiac pacemakers, coronary stents, stents, and/or other cardio vascular implants), shunts, permanent birth control implants, cosmetic implants (e.g., breast implants, pectoral implants, testicular implants, and/or any other cosmetic implants), hernia mesh implants, urogeurogynecologic mesh implants, dental implants (e.g., endosteal, subperiosteal, and/or any other dental implants), implantable gastric stimulators, diaphragmatic/phrenic nerve stimulator implants, resorbable implants, sensors, couplers, and/or any other suitable implant or implants. In some instances, however, the term implant may refer to one or more orthopedic implants (e.g., femoral knee prosthetics, tibial knee prosthetics, hip replacements, and/or any other suitable orthopedic implant).

As used herein, the term contaminants and variations thereof may refer to any material that is desirably removed from, killed, treated, disrupted, broken up, and/or otherwise reduced in a patient, and that can be reduced in the patient through the use of one or more embodiments of the described systems and methods. Some examples of contaminants, include, but are not limited to, one or more infections, bacteria, planktonic bacteria, biofilms, fungi, foreign material, foreign organisms, loose bone cement, shavings, loose tissue, loose cells, pus, lymph, germs, pathogens, viruses, bone flecks, debris, pollutants, clots, anaerobes, microbes, microorganisms, parasites, and/or any other types of material that are desired to be removed from and/or reduced in a patient and that are capable of being removed or reduced with the assistance of the described systems and methods. In some cases, contaminants comprise bacteria (e.g., biofilm and/or planktonic bacteria). More specifically, in some cases, contaminants comprise pathogens such as one or more of the ESKAPE pathogens (e.g., *Enterococcus faecium, Staphylococcus aureus, Klebsiella pneumonia, Acinetobacter baumannii, Pseudomonas aeruginosa*, and/or *Enterobacter* species), which can be among the leading nosocomial (i.e., hospital acquired) infections acquired by patients as a result of a joint operation.

As used herein, the term antimicrobial and variations thereof may refer to any material that is suitable for use in a patient and that is capable of killing contaminants, preventing contaminants from reproducing, reducing a rate at which contaminants reproduce, and/or otherwise reducing contaminants in a patient when used in accordance with the described systems and methods. Some examples of suitable antimicrobials include, but are not limited to, one or more: antibiotics (e.g., penicillin, vancomycin, ofloxacin, aminoglycosides, amoxicillin, ampicillin, erythromycin, cephalexin, and/or any other suitable antibiotics), antifungals (e.g., nystatin, mafenide acetate, and/or any other suitable antifungals), microbicides, biostatic agents, antimicrobial chemotherapy, disinfectants, antivirals, active infused clarifying products, neuraminidase inhibitors, oseltamivir, antiseptics, non-pharmaceutical antimicrobials (e.g., lactic acid, acetic acid, citric acid, one organic acid salts, etc.), synthetic antimicrobials (e.g., sulphonamides, fluoroquinolones, etc.), ozone, ozone solutions, iodine solutions, dilute iodine solutions, alcoholic iodine solutions, aqueous iodine solutions, iodine hydrogels, copper-iodine-complex solutions, alcohols (e.g., ethanol, isopropyl alcohol, and/or any other suitable alcohol), polyhexanide (PHMB), bactericidal agents, bacteriostatic agents, potassium permanganates, peroxycarboxylic acids, phenolics, essential oils, enzymes (e.g., one or more proteinases and/or any other suitable enzyme), chlorhexidine gluconates, anti-parasitics, hypochlorous acids (HOCl), hydrogels, antimicrobial metals (e.g., silver; gold; copper; zinc; one or more biocompatible heavy metals, cationic metals, and/or anionic metals; and/or any other suitable antimicrobial metal or metals), antimicrobial metal alloys, and/or other suitable antimicrobials. In some cases, the antimicrobial comprises one or more copper-iodine-complex solutions that: comprise any suitable amount of iodine that allows free iodine in the solution to remain below its solubility factor (e.g., less than about 330 ppm iodine), are highly effective against antimicrobials (e.g., having greater than a Log 4 kill rate), and/or have little to no cytotoxicity. Indeed, in some embodiments, at least one of the antimicrobials used in accordance with the described systems and methods comprise one or more copper-iodine-complex solutions (where the free iodine remains below its solubility factor to provide a non-cytotoxic but highly efficacious antimicrobial), as produced by Clyra Medical Technologies Inc. of Westminster, Calif., USA.

Additionally, the antimicrobials can be in any suitable form that can be used in accordance with an embodiment described herein, including, without limitation, as a fluid (e.g., liquid, gas, gel, and/or any other suitable fluid), as a powder, as a solid, as micronized particles, as nanoparticles, and/or in any other suitable form. In some cases, however, the antimicrobials comprise one or more fluids (e.g., liquids and/or gels).

As used herein, the term closed portion of a body, closed portion of skin, closed surface of skin, and variations thereof may refer to a joint, body cavity, organ, and/or any portion of a patient's body that is covered with skin, or even a piece of skin and/or skin graft, that is substantially closed so as to not expose a substantial portion of an implant disposed within the body. In some cases, such term is used to refer to a portion of a patient's body or skin that is substantially closed, with the possible exception of one or more relatively small openings that are formed by a practitioner in accordance with an embodiment of the described methods. In this regard, if a large incision is still healing (e.g., still has stitches) in a portion of the patient, that portion can (in some cases) still be considered to be closed (and the skin to be closed) because some embodiments of the described systems and methods do not require that such incision (or at least not all of it) be reopened (or a new large incision to be made) to substantially expose the implant. Additionally, if a portion of the patient's skin comprises a natural orifice (e.g., a mouth, tear duct, etc.), such portion of the patients skin can (in some cases) be considered to be closed.

The following disclosure of the present invention is grouped into four subheadings, namely "Methods for Reducing Contaminants," "Systems for Reducing Contaminants," "Implants for Reducing Contaminants," and "Representative Operating Environment." The utilization of the subheadings is for convenience of the reader only and is not to be construed as being limiting in any sense.

Methods for Reducing Contaminants

In accordance with some conventional practices, when tissue around an implant in a patient becomes infected, the patient is cut open and the implant is removed and/or replaced. In many cases, however, such a procedure can be painful, be costly, require a relatively long recovery period, reduce mobility for an extended period of time (e.g., permanently), require rehabilitation, and/or otherwise cause significant and unwanted side effects.

In contrast, some embodiments of the described systems and methods are configured to reduce infections and/or other contaminants through a relatively non-invasive procedure. For instance, some embodiments of the described systems and methods are configured to remove, kill, slow proliferation, fracture, break up, remove, and/or otherwise reduce contaminants near an implant in a patient, without requiring the patient to be cut open such that the transplant is substantially exposed. Indeed, some of the embodiments described herein involve making one or more relatively small openings in a patient (e.g., near an implant and/or elsewhere), while otherwise keeping skin around the portion of the patient containing the implant (and/or other portion) closed or at least substantially closed. In some cases, once the openings are formed in the patient (e.g., near the implant), one or more antimicrobials are introduced into and/or allowed to exit the patient through such openings. Accordingly, some embodiments allow contaminants to be killed, flushed from, and/or otherwise reduced in a patient through a relatively non-invasive method.

The described systems and methods for reducing contaminants in a patient can comprise any suitable component and/or feature that allows one or more contaminants to be killed, removed from, fractured, sterilized, and/or otherwise reduced in a patient (i.e., a patient with or without an implant). By way of non-limiting illustration, FIG. 1 shows a representative embodiment of a method 10 for reducing contaminants in a patient. Specifically, FIG. 1 shows that, in some embodiments, the method 10 comprises: identifying a location in the patient that is infected or that is otherwise contaminated (see e.g., box 12), placing one or more openings in the patient (see e.g., box 14), disrupting contaminants in the patient (see e.g., box 16), flushing one or more fluids through one or more of the openings in the patient (see e.g., box 18), flowing one or more antimicrobials into the patient at or near the site of contamination (or potential contamination) (see e.g., box 20), flushing the antimicrobials from the patient (see e.g., box 22), closing the openings (see e.g., box 24), and/or other suitable feature.

With respect to box 12, FIG. 1 shows that some embodiments of the described method 10 include identifying one or more locations in the patient that are infected, that may be infected, and/or that are or may otherwise be contaminated. In this regard, a contaminated site or a potentially contaminated site can be identified (or potentially identified) in any suitable manner, including, without limitation, by: performing a culture, performing a biopsy, identifying localized pain, identifying pain, observing localized redness, identifying an abnormal coloration on a portion of the patient, identifying an abnormal smell associated with a portion of the patient, observing pus and/or other leakage from a portion of the patient, observing redness and/or swelling in a portion of the patient, identifying veins in the patient that are abnormally colored, observing a raised body temperature (generally and/or at a localized portion) of the patient, identifying any clinical sign that may indicate that the patient has an infection, and/or in any other suitable manner.

In some embodiments, contamination or potential contamination is identified (and the described systems and methods are used): in a patient who does not have an implant and/or in one or more locations that are disposed in the patient remotely from any implant. In some other embodiments, however, the described systems and methods are used to reduce contamination in a portion of a patient that comprises an implant (e.g., a knee implant, a hip implant, a breast implant, and/or any other implant). Accordingly, in such instances, swelling, leakage, redness, pain, increased temperature, one or more clinical signs that may indicate the presence of an infection, and/or other possible indications of contamination near an implant (or elsewhere in a patient) are used to identify contamination or potential contamination in a patient.

In some cases, once a practitioner has identified or potentially identified an infection and/or other contamination in the patient, box 14 shows that some embodiments of the method 10 continue as one or more ports, conduits, inlets, outlets, and/or other openings are formed in the patient (e.g., near the contamination and/or potential contamination). In this regard, the openings can be formed in any suitable manner, including, without limitation, via one or more incisions, cuts, stabs, punctures, and/or other suitable methods. Indeed, in some embodiments, the openings are formed by sanitizing a portion of the patient's skin (e.g., with iodine, alcohol, and/or any other suitable disinfectant), shaving a portion of the patient's skin, and/or cutting an opening in the patient's skin. In some particular embodiments, one or more incisions are made with a number 10 blade (and/or any other suitable device of any suitable size) that is punctured into the skin, following which a trocar (and/or any other suitable device) with an optional cannula is introduced into the incision to form the described opening.

In some embodiments (as mentioned), the described method 10 includes forming one or more openings in a portion of the patient that is closed (or substantially closed). Indeed, unlike some competing conventional methods that require one or more relatively large cuts to be made in a patient (e.g., so as to substantially expose an implant in the patient) to treat an internal infection, some embodiments of the described systems and methods allow a practitioner to perform the described methods by only forming one or more relatively small openings in the patient.

As part of the described method 10, a practitioner may form any suitable number of openings in a patient in or near the site of contamination or possible contamination. Indeed, in some embodiments, 1, 2, 3, 4, 5, 6, 7, 8, 9, 10, or more openings are formed in the patient at or near the site of contamination (e.g., near an implant). Indeed, in some embodiments, a single opening is formed at or near the contamination (or potential contamination) site. In some such embodiments, the single opening is configured to act as an inlet into and/or an outlet from the patient. For instance, in some such embodiments, one or more antimicrobial materials and/or other suitable materials (e.g., disrupting materials, rinsing aids, water, tools, cameras, sensors, and/or any other suitable materials) are introduced into and/or removed from the patient through the single opening. In this regard, such materials can be introduced and/or removed from an internal space in the patient via a single conduit through, a first and a second lumen, multiple conduits, and/or in any other suitable manner. Thus, in some embodiments, the single opening acts as an inlet and/or an outlet to the patient (e.g., to a portion of the patient that comprises, or is at least suspected of comprising, contamination) so as to allow the described systems and methods to be effectuated in a relatively non-invasive (or minimally invasive) manner.

Figure 2:
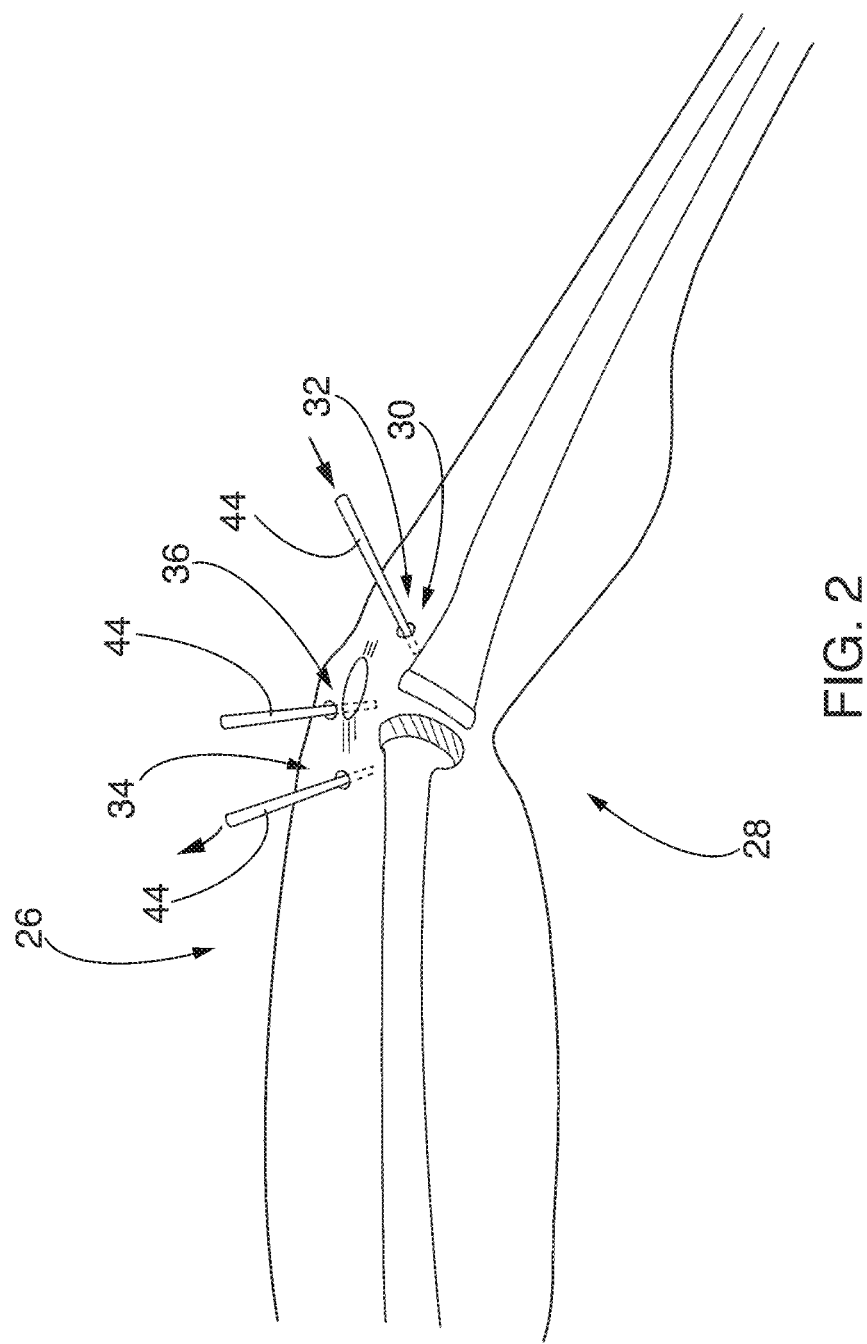
FIG. 2 illustrates a portion of a patient comprising multiple openings near an implant in accordance with a representative embodiment.

In some other embodiments, the method 10 includes forming two or more openings in the patient (e.g., at or near an implant and/or contamination site). In some such embodiments, one or more openings serve as inlets to allow one or more antimicrobials, contaminant disruption materials, tools, sensors, and/or any other suitable materials or objects to be introduced into the patient through the openings. In some embodiments, one or more openings further serve as outlets to allow one or more antimicrobials, contaminant disruption materials, and/or any other suitable materials or objects to be released from the portion of the patient that is being treated. In some embodiments, however, an opening is configured to act (or acts) as both an inlet and an outlet (e.g., as described above). In still other embodiments, one opening serves as a fluid inlet into the internal space, another opening serves as a fluid outlet to the internal space, and a third and/or fourth opening provides one or more of a camera, ultrasonic vibrating head, scouring pad, and/or other tool with access to the internal space. In one non-limiting illustration, FIG. 2 shows a patient's leg 26 and knee 28 having multiple openings 30 (e.g., 3) defined or disposed therein. In particular, FIG. 2 shows an embodiment in which a first opening 32 serves as an inlet and a second opening 34 serves as an outlet.

Thus, in some such embodiments, the antimicrobial (and/or any other suitable material or object) can flow (and/or otherwise be placed) into and then out of the patient (or a closed portion of the patient). As a result, in some cases, contaminants (e.g., bacteria, planktonic bacteria, biofilm, tissue, cells, fungi, spores, shavings, debris, drainage, pus, and/or any other contaminants) can be flushed from the patient, a contaminated portion of patient can be irrigated, fresh antimicrobial can be continuously introduced into the contamination site, one or more abrasive materials can optionally flow through (and not necessarily be left in) the contamination site, one or more materials can be introduced into a pressurized capsule within the patient, and/or other materials and/or objects can otherwise be introduced into the contamination site through one or more openings 30 and then (in some cases) be released from the patient through one or more other openings in the closed portion of the patient's skin.

Additionally, FIG. 2 shows an embodiment in which one or more additional openings (e.g., a third opening 36) serve as an inlet and/or an outlet to allow one or more instruments, tools, cameras, light sources, sensors, objects, fluids, electrodes, vibrating heads, brushes, microfluidics, and/or other materials or objects to be introduced into and/or removed from the patient (e.g., through the same and/or a different opening). Indeed, in some embodiments, one or more openings are configured to allow one or more cameras, arthroscopes, arthroscopic tools, arthroscopic ultrasonic tools, arthroscopic low frequency tools, shavers, scrapers, cauterizers, vibrating brushes, laparoscopes, laparoscopic tools, suction tools, vibrating heads, brushes, deburring tools, tools, tubes, electrodes, and/or other instruments or materials to be introduced into (and removed from) the patient at or near a site of contamination or potential contamination. Accordingly, in some such embodiments, one or more fluids or other materials are able to flow through the contamination site (e.g., via one or more inlets 32 and outlets 34) while a practitioner can watch what is happening inside the contaminated site and/or scrape, brush, deburr, clean, manipulate, cut, cauterize, shave, provide electrical current to, suck, apply pressure to, and/or otherwise contact or treat surfaces and/or features within the patient.

In some embodiments, the described method 10 includes inserting one or more cameras into the internal space (e.g., through an opening 30) to allow a practitioner to observe the internal space. Indeed, in some embodiments, one or more arthroscopic cameras are inserted into the internal space to allow a practitioner to watch conduit placement, tool placement, to observe tissue conditions, to visually identify contaminants, and/or to perform any other suitable function.

Indeed, in accordance with some embodiments, the described method 10 includes inserting one or more microfluidics, sensors, and/or cameras that are configured to identify bacteria and/or biofilm (e.g., one or more digital cameras, steerable cameras, arthroscopic cameras, infrared cameras, blue light cameras, ultraviolet light illumination cameras having a dual bandpass (and/or any other suitable) optical filter that is configured to detect fluorescence and/or other characteristics of bacteria or biofilm, cameras that are configured to identify bacteria and/or other contaminants via fluorescence, cameras that are capable of imaging in multiple wavelengths, and/or any other suitable camera or sensor that is capable of detecting and/or quantifying bacteria and/or biofilm in a patient in real time or near real time) through one of the openings 30 and into an internal space in the patient. Indeed, in some embodiments, such a camera comprises an arthroscopic camera that is configured to qualitatively and quantitatively identify bacteria and/or biofilm in a portion of a patient (e.g., in the internal space).

In some embodiments, use of such a camera (and/or other sensor device) that is configured to readily detect and/or quantify bacteria and/or biofilm allows a practitioner and/or processor to readily detect bacteria and/or biofilm within the internal space and to then take measures to remove or otherwise reduce such contaminants in the internal space. For instance, in some instances where a practitioner identifies bacteria and/or other contaminants in a certain area within an internal space, the practitioner can apply ultrasonic vibrations to, flush, use mechanical debridement, and/or otherwise work to break up such bacteria and/or biofilm and to remove it from the internal space (e.g., as discussed below) or to reduce it to a level deemed acceptable to allow subsequent healing.

Figure 3:
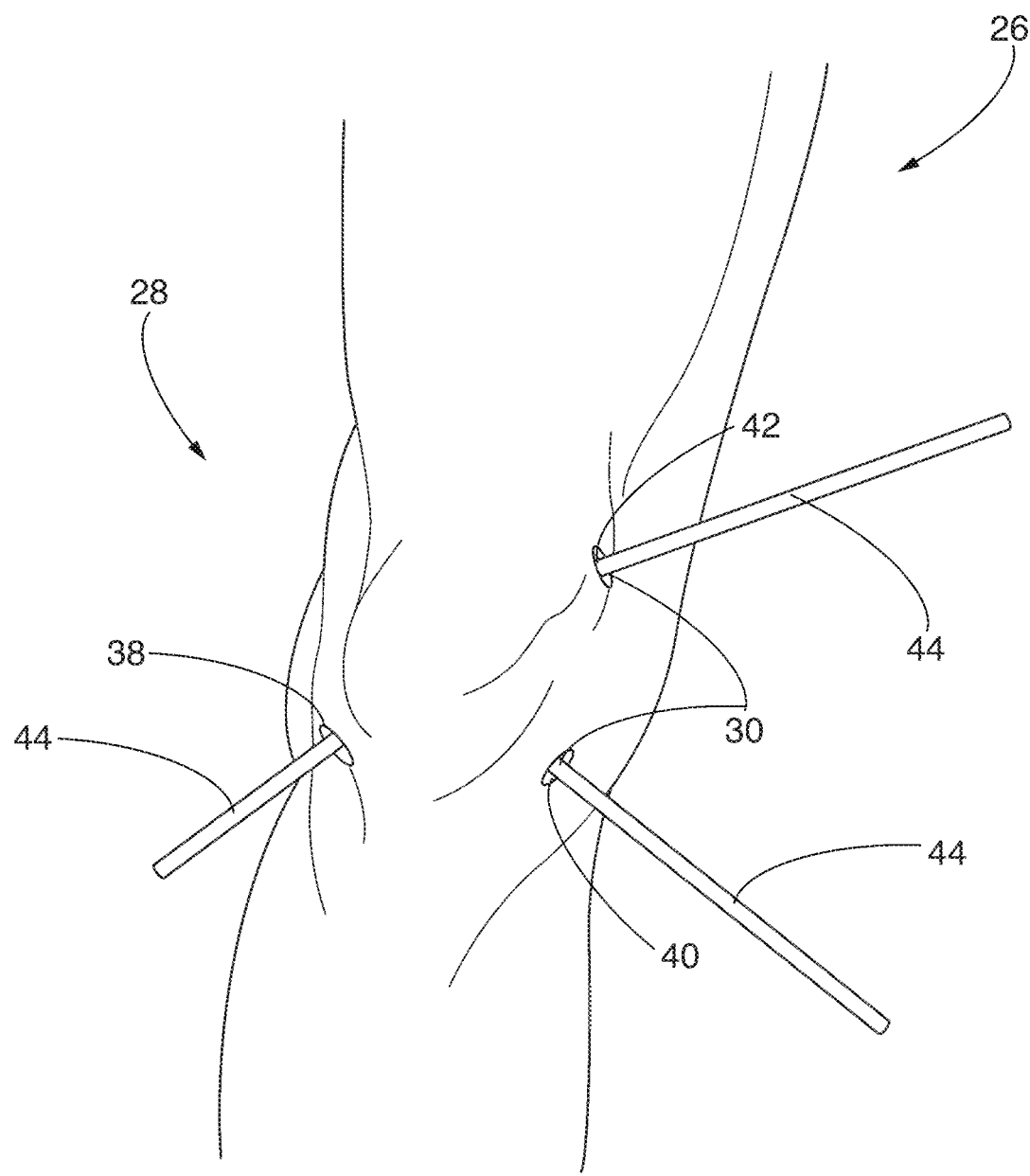
FIG. 3 illustrates a partially transparent view of a patient's knee in accordance with a representative embodiment of the described systems and methods.

Continuing with the discussion of the openings 30, the openings (e.g., the relatively small openings in the closed portion of the patient's skin) can be placed in the patient in any suitable location with respect to the contaminated portion (or suspected contaminated portion) of the patient. In some embodiments, one or more openings are placed in the center of, lateral to, medial to, superior to, inferior to, superomedial to, superolateral to, inferalateral to, inferomedial to, and/or in any other suitable location with respect to the contaminated (or suspected contaminated) portion of the patient. By way of non-limiting illustration, FIG. 3 shows an embodiment in which a patient's knee 30 comprises an inferalateral opening 38, an inferomedial opening 40, and a superomedial opening 42.

While the openings 30 can be any suitable size that allows the described systems and methods to function as described herein, in some embodiments, each of the openings has a diameter (or a width, length, and/or height) that is between about 0.18 mm and about 3 cm (or that falls in any subrange thereof). Indeed, in some embodiments, the openings are less than about 1.5 cm in diameter (or width, length, and/or height) (e.g., 6 mm±4 mm).

Additionally, in some embodiments, one or more of the openings 30 are sized and shaped to substantially contact an outer surface (e.g., an entire perimeter of an outer surface) of one or more straws, cannulas, lumens, ports, tubes, catheters, and/or other conduits or objects that extend through the patient's skin. Thus, in some embodiments, the openings are relatively small and allow a practitioner to reduce contaminants in a patient without necessarily having to: cut a large incision in the patient, substantially expose an implant, remove the implant, and/or replace the implant. Additionally, in some cases, by making the openings relatively small, the described methods can result in little to no undue amounts of leakage between the skin defining an opening and the conduit in the opening. In any case, in some embodiments, the practitioner leaves the patient's skin around the contaminated (or potentially contaminated) site completely or substantially closed (or the practitioner does not form additional holes in the patient's skin), with the exceptions of the openings.

In some embodiments, no tube, conduit, and/or instrument is placed (at least not initially) in one or more of the openings 30 (e.g., such that fluids can flow directly out of the openings). In some other embodiments, however, once one or more of the openings are formed in a patient, one or more cannulas, tubes, ports, grommets, rings, eyelets, catheters, sheaths, and/or other conduits comprising one or more types of plastic, polymer, metal, ceramic, rubber, synthetic materials, natural materials, and/or other suitable materials are placed in one or more of the openings. Thus, in some embodiments, the openings are kept open and the conduits can readily allow fluids, gels, beads, instruments, tools, brushes, vibrating brushes, shavers, ultrasonic heads, electrolytic tools, electrodes, conduits, cameras, sensors, and/or other objects or materials to be introduced into (and/or to be removed from) the patient (e.g., the contaminated portion of the patient and/or the portion of the patient comprising an implant). By way of non-limiting illustration, FIGS. 2-3 show some embodiments in which one or more conduits 44 are disposed in the openings 30 in the patient.

In some embodiments, the conduits 44 are configured to remain open (e.g., to allow fluids, objects, and/or other suitable materials to pass through the conduits) as long as the conduits are in the openings 30. In some other embodiments, however, one or more of the conduits (or openings) are configured to be selectively opened and closed (or occluded) so as to: prevent fluids and/or materials from leaving the body, slow a rate at which fluids and/or materials leave the body, increase or otherwise control dwell time of an antimicrobial or other material inside of the patient, allow the patient to keep the conduits in the patient's skin between treatments, prevent contaminants from entering into the conduits when they are closed (e.g., between treatments), allow an increased amount of fluid to be retained in a portion of the patient for a desired period of time, allow for a pressurized capsule to be formed near the implant and/or in the internal space (e.g., allow the internal space to be expanded or inflated), and/or for any other suitable purpose.

Where the conduits 44 are configured to selectively open and/or close (or to otherwise be occluded), the conduits can comprise any suitable component that allows them to function in such a manner. Indeed in some embodiments, one or more of the conduits comprise one or more valves, one-way valves, two-way valves, crimps, clamps, pinches, stop cocks, clips, roller clamps, clamps, caps, lids, closures, plugs, corks, and/or any other suitable components that are configured selectively or permanently close a conduit.

Returning again to FIG. 1, box 16 shows that some embodiments of the method 10 optionally include disrupting contaminants in the patient (e.g., at the contamination site and/or near an implant). In this regard, some contaminants, such as biofilm, can be relatively hard to break up and can be difficult for antimicrobials to kill. In this regard, some biofilms protect bacteria such that bacteria in biofilm can continue to grow, even in the presence of a potent antimicrobial. Accordingly, by disrupting the contaminants, some of the contaminants can be: killed, broken loose so that they can be flushed from the patient, loosened so that they are accessible to the antimicrobial, and/or otherwise reduced in the patient.

Where contaminants in the patient are loosened, broken up, and/or otherwise disrupted, the contaminants can be disrupted in any suitable manner. In some embodiments, one or more contaminant disruption chemicals are introduced into the contaminated (or potentially contaminated) site. Some non-limiting examples of such contaminant disruption chemicals include one or more: acids (e.g., acetic acid, hyaluronic acid, tannic acid, citric acid, hypochlorous acid, an acidic solution having a pH between about 2 and about 6.9 (or in any subrange thereof), and/or any other suitable acid that is capable of disrupting contaminants), bases (e.g., a basic solution having a pH between about 7.1 and about 10 (or any subrange thereof) and/or any other suitable base that is capable of disrupting contaminants in a patient), glu- dahydes, iodine compounds, chlorhexadines, silver deriva- tives, alcohols (e.g., ethanol, isopropyl alcohol, and/or any other suitable alcohols), surfactants (e.g., tween, benzalko- nium chloride, and/or any other suitable surfactants), enzymes (e.g., proteases and/or any other suitable enzymes), antimicrobials (e.g., as discussed below), carrier agents, bio-disruptors, gel substances, and/or any other suitable chemicals that are configured to disrupt contaminants by being introduced into a contaminated portion of the patient through one or more openings 30. Indeed, in some embodi- ments, a disrupting chemical comprising ethanol, acetic acid, sodium acetate, benzalkonium chloride, saline solu- tion, and/or water is introduced into the contaminated sited via one or more openings 30.

Where one or more contaminant disruption chemicals are introduced into an inner space of a contaminated site (e.g., via the openings 30) in a patient, the chemicals or other materials can be introduced in any suitable manner, includ- ing, without limitation, by being injected under pressure into and/or through the internal space; by being pulsed (e.g., injected with intermittent pressure) into and/or through the internal space; by being continuously introduced into and released from the contaminated site; by irrigating the con- taminated side through the patient's closed skin; by being gravity flowed into the patient; by being allowed to dwell internally in the contaminated site for a period of time; through a process that provides the chemicals or other materials with a laminar flow into and/or within an internal space of the patient; through a process that provides the materials with a hydrostatic flow into and/or through the internal space; through a process that provides the materials with a hydraulic flow into and/or through the internal space; through a process that provides the chemicals or other materials with a turbulent flow into and/or through the internal space; through a process that provides varied pres- sure to the chemicals as then enter, dwell within, and/or exit the internal space; through a process that provides suction (e.g., intermittent suction, constant suction, variable suction, suction interspersed with increased pressure, and/or any other suitable type of suction) to the chemicals; and/or in any other suitable manner. Indeed, in some embodiments, the contaminant disruption chemicals are introduced into the patient through one or more of the openings with the use of a pulse lavage apparatus that is configured to deliver one or more chemicals into an internal space in the patient.

In some embodiments, the contaminant disruption chemi- cals (and/or any other suitable materials, such as an antimi- crobial) are injected or otherwise caused or allowed to flow into an internal space of the patient under pressure such that the internal space inflates and the materials are able to flow throughout the internal space. In some such embodiments, the materials are then allowed to remain or dwell in the internal space of the patient for any suitable amount of time (e.g., for between 0 seconds about 8 hours, or within any subrange thereof). Moreover, in some such embodiments, some or all of the chemicals (or other materials) are sucked out, pressed out, flushed, allowed to drain, and/or otherwise removed from the internal space in the patient.

Furthermore, in some embodiments, the process of flow- ing one or more chemicals (or other materials) into the internal space and then removing such chemicals from the internal space is repeated any suitable number of times. Indeed, in some embodiments, one or more chemicals are injected (or otherwise flow) into the internal space under pressure, with such chemicals being allowed to dwell in the inflated internal space for a desired period of time, and then some or all of the chemicals are flushed, drained, and/or otherwise removed from the internal space. Although in some such embodiments, one type of material (e.g., con- taminant disruption chemical) is forced into and removed from the internal space multiple times, in some other cases, two or more different types of materials (e.g., a contaminant disruption chemical, an antimicrobial, a rinsing fluid, and/or any other suitable material or materials) are flowed into and out of the internal space, either together or at separate times. Additionally, although this process, whether repeated or not, can take place over any suitable period of time, in some embodiments, it is accomplished during the duration of a single surgery (e.g., a single surgical procedure) on the patient. Indeed, in some cases, this process of inflating and deflating the internal space one or more times can take place in any suitable period of time, including, without limitation, in less than about 8 hours (e.g., less than about 2 hours).

In some embodiments, after being introduced into an internal space (or volume) of the contaminated site, the contaminant disruption chemicals (or other materials, as discussed below) are allowed to dwell in the space (which is sometimes enlarged by the materials added into the internal space) for any suitable amount of time that allows them to perform their intended purpose. In some cases, the contami- nant disruption chemical is allowed to dwell in the internal space of the contaminated portion of the patient for between about 0.5 seconds and about 7 days, or within any subrange thereof. For instance, in some embodiments, one or more disrupting chemicals are allowed to dwell within an internal space of the contaminated site (e.g., so as to contact an implant and/or tissue adjacent to the implant) for more than about 10 seconds (e.g., more than about 10 minutes or more than about 30 minutes). In some embodiments, the entire process (e.g., from forming the openings 30, to reducing contaminants in the patient (e.g., via application of the contaminant disruption chemical, the antimicrobial, etc.) and to closing the openings) takes place in during a single surgical procedure. Indeed, in some embodiments, the entire method takes place in less than about 8 hours (e.g., in less than about 2 hours).

In some embodiments, the process of disrupting contami- nants in the contaminated (or potentially contaminated) portion of the patient involves one or more mechanical processes in which the contaminants, internal surfaces of the patient, and/or external surfaces of the implant are brushed, abraded, rubbed, scoured, rasped, scraped, swabbed, wiped, buffed, massaged, pulsed, treated with electrical current, and/or otherwise contacted in such a way as to at least partially disrupt contaminants (e.g., break up biofilm, disrupt planktonic bacteria, and/or otherwise disrupt contaminants) in the patient. Indeed, in some embodiments, one or more brushes, deburring tools, scouring pads, arthroscopic tools, debrisan beads, abrasive materials, dextranomer solutions, dextranomer beads, salts, and/or other suitable objects and/ or materials that are capable of breaking up and/or otherwise disrupting contaminants are moved into an internal space of the contaminated portion of the patient through one of the openings 30.

Indeed, in some embodiments, a camera (e.g., as dis- cussed above) and cleaning tool (e.g., brush, scouring pad, vibrating cleaning tool, vibrating brush, and/or any other suitable cleaning tool) are introduced into an internal space of the contaminated portion of the patient, through one or more of the openings 30, and one or more internal surfaces of the contaminated portion of the patient and surfaces of an adjacent implant are scrubbed (e.g., so as to break up biofilm). In some other embodiments, however, one or more abrasive materials (e.g., debrisan beads) are flowed into and removed from the internal space of the contaminated portion. In some other embodiments, such abrasive materials are configured to be resorbed into the patient, such that they are abrasive for a short period of time, after which they begin to dissolve and/or to be resorbed by the patient's body. In this manner, if any abrasive material is left behind in the patient, it will not continue to abrade for a significant period of time. In this regard, such a resorbable abrasion material can include, without limitation, one or more salts, gels, powders (e.g., iodine powders), solutions comprising any of the foregoing, and/or other suitable abrasive materials.

As another example of a process for disrupting contaminants in the contaminated (or potentially contaminated) portion of the patient, in some embodiments, a fluid (e.g., water, saline solution, contaminant disruption chemical, antimicrobial, gel, hydrogel, solution comprising one or more abrasive materials (e.g., debrisan beads), and/or other suitable material) is introduced into an internal space of the contaminated portion of the patient under pressure. In this regard, any such material can be introduced into the internal space at any suitable pressure.

Indeed, in some embodiments, such materials (e.g., one or more disrupting chemicals, antimicrobials, rinsing agents, etc.) are introduced into the internal space under a pressure that allows such materials to have a laminar, hydrostatic, and/or hydraulic flow as they enter the patient through an opening 30, as they flow through and/or dwell in an internal space of the patient, and/or as they flow out of the patient through an opening. In some other embodiments, however, such materials are introduced into the internal space of the contaminated portion under a pressure that causes such materials to have a turbulent flow as they enter the patient through an opening, as they flow through an internal space of the patient, and/or as they flow out of the patient through the opening. In still other embodiments, pressure is modified such that the material's flow is laminar (or hydrostatic) and turbulent at different times. Additionally, in some embodiments, such materials are introduced into an internal space in the patient via a steerable nozzle that allows a practitioner to direct the materials to a desired location in the patient (e.g., as identified via a camera and/or any other suitable sensor).

In some cases, the contaminant disruption (and/or any other suitable portion of the method 10, including without limitation, flushing (as shown at box 18 in FIG. 1), the antimicrobial treatment (as shown at 20), flushing the antimicrobial (as shown at 22), and/or any other suitable part of the method) is performed through (or includes) use of one or more types of vibrations, which can include, but are not limited to, ultrasound, low frequency ultrasound, ultra-low frequency ultrasound, regular frequency ultrasound, sonic, contact, non-contact, and/or any other suitable form of ultrasound and/or sonic vibrations.

While this application of vibrations to an internal space can be accomplished in any suitable manner, in some embodiments, one or more ultrasonic (and/or sonic) heads and/or interfaces are inserted through one or more of the openings 30 and into the inner space within the patient (e.g., a space comprising contamination). In some cases, water, saline, an antimicrobial, a contaminant disruption chemical, a gel, and/or any other suitable medium is disposed around the ultrasonic and/or sonic head. As a result, when the head vibrates, it tends to break up biofilm, liquefy biofilm, kill microbes, break up planktonic bacteria, heat up and damage contaminants, break up polysaccharide and/or other connections between bacteria, break up bacterial cell walls, and/or to otherwise disrupt contaminants such that the contaminants can: better be treated with an antimicrobial, better be flushed out of the patient, be killed, be disrupted, and/or otherwise be reduced in the patient. In some cases, as the head vibrates, it allows the antimicrobial (or other chemicals) in the internal space to have better access to contaminants, to be heated, and/or to otherwise be more efficacious that it would be without the vibrations.

Figure 5A:
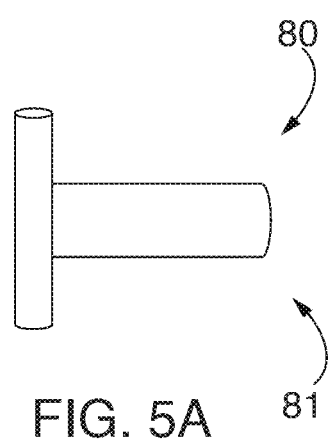
FIGS. 5A-5E illustrate views of different representative embodiments of vibrating heads that are configured to be inserted into a closed portion of a patient.
Figure 5B:
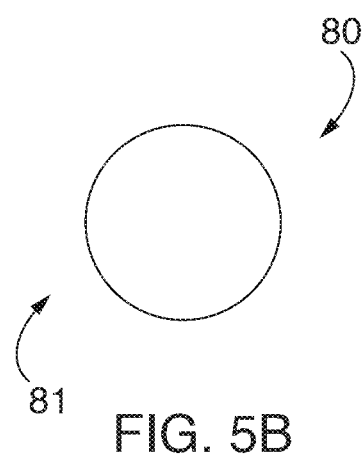
Figure 5C:
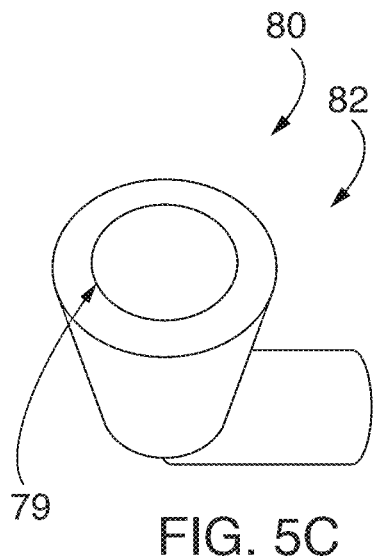
Figure 5D:
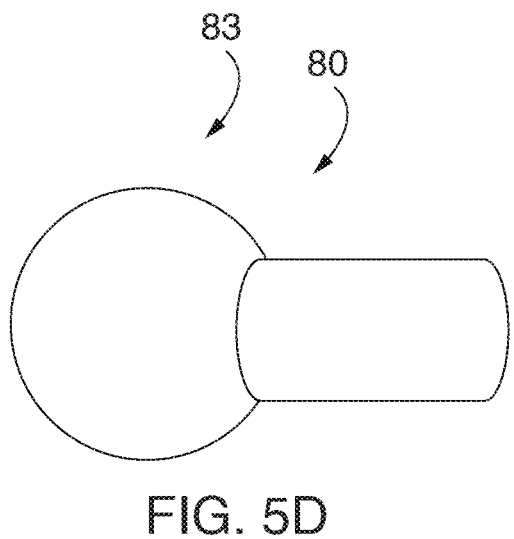
Figure 5E:
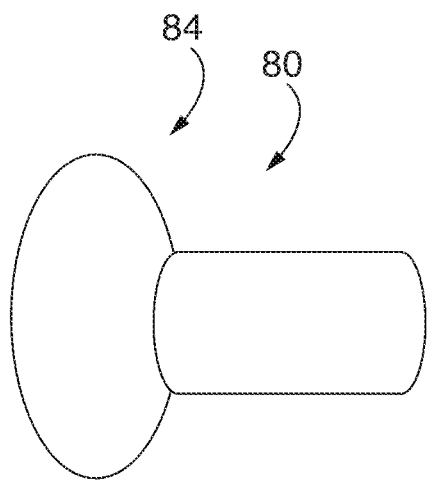

While the vibrations applied to materials (e.g., contaminant disruption chemical, the antimicrobial, the rinsing agent, etc.) within an internal space of a patient can be performed at any suitable frequency, in some cases, they occur at between about 5 kHz and about 100 MHz, or within any subrange thereof (e.g., between about 30 kHz and about 1.5 MHz). In some cases, however, such sonic stimulation takes place at between about 20 kHz and about 1 MHz, or within any subrange thereof (e.g., between about 20 kHz and about 80 kHz). Additionally, while in some embodiments, the frequency of the vibrations remains relatively constant during one or more portions of the described method 10, in some other embodiments, the frequency of such vibrations can be modified in any suitable manner throughout one or more portions of the method.

Where ultrasound is used to provide contaminant disruption (and/or at any other suitable portion of the method 10), an ultrasound emitting device can have any suitable characteristic that allows it to disrupt contaminants, increase antimicrobial efficacy, provide heat to the internal space, and/or perform any other suitable function. Indeed, in some cases, the ultrasound (and/or sonic) emitting device comprises one or more soft, firm, hard, resilient, flexible, cannulated, smooth, roughened, ridged, straw-shaped, rod-shaped, filament-shaped, and/or any other suitable type of heads or interfaces.

Where an ultrasound emitting device is used with an embodiment of the described method, such device can comprise any suitable head shape and/or characteristic, including, without limitation, being rounded, squared, cylindrical, conical, cavitated, spherical, circular, elliptical, pointed, symmetrical, asymmetrical, and/or being any other suitable shape and/or being rigid, being resilient, being steerable, being flexible, and/or having any other suitable characteristic that allows it to provide vibrations to an internal space of the patient. By way of non-limiting illustration, FIGS. 5A-5E illustrate some non-limiting examples of suitable vibrating (e.g., sonic or ultrasonic) heads 80. Specifically, FIGS. 5A-5B show some embodiments of a circular head 81. FIG. 5C illustrates an embodiment of a cavitative head 82 (e.g., a head that is configured to cause chaotic motion in (and to thereby) break up bacterial cell walls). In particular, FIG. 5C shows an embodiment in which the head comprises a recessed portion 79. Additionally, FIG. 5D illustrates an embodiment of a spherical head 83 (e.g., for providing entire joint coverage and/or for any other suitable purpose). FIG. 5E further illustrates an embodiment of a conical or elliptical head 84 (e.g., for providing relatively good targeting for a capsule within the patient and/or for any other suitable purpose).

Where an ultrasonic head 80 is inserted into a closed portion of a patient (e.g., via an opening 30), the head can have any suitable diameter, width, length, and/or other measurement that allows it to be inserted through one of the openings 30 and into (and to operate within) the closed portion of the patient. Indeed, in some embodiments, the ultrasonic head has a diameter (or width) that is between about 0.16 mm and about 2.8 cm (or that falls within any subrange thereof). Indeed, in some embodiments, a portion of the ultrasonic head that is configured to extend into an opening in the closed portion of the patient is less than about 1.2 cm in diameter (or width) (e.g., being about 5 mm±3 mm).

As another example of a suitable technique for contaminant disruption, in some cases, such disruption (and/or any other suitable portion of the described method 10, including, without limitation, flushing and antimicrobial treatment) is accomplished by applying mechanical stress energy and/or electromagnetic energy to the contaminants and/or to materials within the internal space being treated. Indeed, in some such cases, one or more photo-acoustic treatment devices comprising an ultrasound transducer, a light source, and/or photo-acoustic element is inserted into the patient through one of the openings 30 in the patient's closed skin to disrupt contaminants (e.g., biofilm) within the patient (e.g., near an implant). In this regard, as such photo-acoustic treatment is performed, contaminants (e.g., biofilm) are broken up, killed, and/or otherwise disrupted.

In some cases, contaminant disruption in the patient (and/or any other suitable portion of the method 10) is accomplished by inserting an electric field producing device into the patient through one or more of the openings 30. In some such cases, in addition to (or in place of) introducing ultrasonic (or sonic) energy into the patient (e.g., as discussed above), some embodiments of the method comprise using one or more electrodes that are configured to create an electric field that is configured to heat a portion of the internal space, disrupt biofilm and/or other contaminants in the patient (e.g., on or near the implant), and/or to otherwise allow one more materials in the internal space (e.g., the contaminant disruption chemical, the antimicrobial, etc.) to be more efficacious.

In accordance with some embodiments, contaminant disruption (and/or any other suitable portion of the method 10) is accomplished in any suitable electrical manner. Indeed, in some cases, one or more moisture-activated microcell batteries comprising elemental silver and elemental zinc (and/or any other suitable components) are introduced into the patient (e.g., through one or more openings in the closed portion of the patient's skin) to: electrostatically stress microbes, disrupt microbe communication, and/or to otherwise disrupt contaminants in the patient.

In some additional embodiments, the contaminant disruption (and/or any other suitable portion of the method 10) is accomplished with the use of ultraviolet light. Indeed, in some embodiments, one or more ultraviolet lights are inserted through one of the openings 30 and into the patient to kill and/or otherwise disrupt contaminants in the patient.

In still additional embodiments, contaminants are disrupted by (and/or any other suitable portion of the method 10 includes): introducing carbon technology into the internal space through one or more of the openings 30 to use Van der Waals forces to kill and/or reduce contaminants in the internal space, applying a radioactive material into the internal space through one or more of the openings, exposing the contaminants to electrostatic charges, exposing the contaminants to magnetic fields, exposing the contaminants to electrolysis and/or electrolyzed materials, performing a synovectomy, and/or in any other suitable manner (including in through any combination of the methods for contaminant disruption and or other portions of the method 10 described herein). While such modifications and/or the other methods disclosed herein can have several features, in some embodiments, by performing one or more of the methods described herein, such methods can prevent regrowth of biofilm and/or other contaminants, can be relatively safe, and/or can reduce the chances that implant replacement will be required (e.g., in post-infected total knee replacements and/or elsewhere).

In some instances, the described contaminant disruption (and/or any other suitable portion of the described method 10) is accomplished by having one or more active electrodes be placed within the patient (e.g., via one or more openings 30 in the patient near an implant); placing an electrically conductive fluid in the patient, near the active electrode; and applying a high frequency voltage between the active electrode and a return electrode in the presence of the electrically conductive fluid to generate an ionized vapor and/or liquid layer at the active electrode. In some such instances, the ionized vapor that is formed is configured to sterilize and/or otherwise disrupt biofilm and/or other contaminants in the patient (e.g., near the implant).

In some additional embodiments, the contaminant disruption (and/or any other suitable portion of the method 10) includes providing heat to the internal space. In this regard, such heat can be provided to the internal space in any suitable manner, including, without limitation, through the use of one or more heaters, heating pads, heated fluids, and/or other heating mechanisms that are disposed (partially or otherwise) within and/or without the internal space. Indeed, in some embodiments, the contaminant disruption chemical (and/or any other suitable material, such as the antimicrobial and/or rinsing agent) is heated. In some such embodiments, such heating can: help the contaminant disruption chemical (and/or any other suitable material) better break down or reduce contaminants, help increase blood flow at and around the internal space, and/or can otherwise improve the efficacy of one or more portions of the described method 10.

Where the internal space and/or one or more materials that are introduced into the internal space are heated, such space and/or materials can be heated to any suitable temperature, including, without limitation, to between about 34° C. about 52° C. (or within any subrange thereof). Indeed, in some embodiments, the internal space and/or one or more materials that are introduced to the internal space are heated to between about 34° C. and about 40° C.

With reference now to box 18, FIG. 1 shows that some embodiments of the described methods 10 optionally include rinsing, washing, and/or otherwise flushing one or more fluids through one or more of the openings 30 and the internal space to remove one or more: contaminants, contaminant disruption chemicals, abrasive materials, debris, loose tissue, and/or other materials or objects in the patient. In this regard, any suitable material can be flushed through the patient, including, without limitation, water, a saline solution, an antimicrobial, the same or a different contaminant disruption chemical, an ozone solution, and/or any other suitable material. Indeed, in some embodiments, after a contaminant disruption chemical is flowed through an internal space in the patient, a saline solution is used to flush and rinse the disruption chemical from the internal space.

Where the internal space in a patient is rinsed and/or otherwise flushed after contaminant disruption, such flushing can occur in any suitable manner (including, without limitation, in any manner that the contaminant disrupting chemical can be introduced into and/or be removed from the internal space, as discussed above). Indeed, in some embodiments, the rinsing or flushing agent (e.g., water, saline, an antimicrobial, a disruption chemical, a gel, and/or any other suitable fluid) is: used to inflate and/or deflate the internal space (e.g., once or multiple times); flowed through one or more of the openings 30 into and/or through the internal space with a hydrostatic and/or laminar flow; flowed into and/or through the internal space with a turbulent flow; jetted into and/or through the internal space; intermittently flowed into and/or through the internal space; continuously and/or continually flowed through the internal space; sucked through and/or from the internal space (e.g., intermittently, alternating with an increased pressure, and/or in any other suitable manner); allowed to dwell within the internal space for any suitable amount of time, including, without limitation, between about 0.1 second and about 24 hours, or within any subrange thereof (e.g., between about 1 second and about 60 seconds); flowed through the internal space via a pulsed lavage through one or more of the openings; flowed through the internal space via a lavage technique; gravity flowed; flowed so as to imitate normal fluid flow to a joint; removed from the internal space through suction (e.g., from a negative pressure wound therapy device, a vacuum, an aspirator, and/or any other suitable device or technique), and/or is otherwise flowed through the internal space.

Although some embodiments of the flushing set forth in box 18 of FIG. 1 simply include flushing materials from the internal space, some other embodiments of the flushing process include any other suitable step or procedure that helps to remove materials and/or contaminants in the internal space. By way of non-limiting example, some embodiments of the flushing set forth at box 18 include applying vibrations to fluids in the internal space, heating flushing agents, providing electrical charges to the flushing agents, using the flushing agents to repeatedly inflate and/or deflate the internal space, and/or otherwise applying any of the features of the contaminant disruption process (e.g., as described above) to the flushing process.

Turning now to box 20, FIG. 1 shows that some embodiments of the method 10 include flowing one or more antimicrobials through one or more openings 30 and into the internal space within the patient. In this regard, any suitable antimicrobial (or combination of antimicrobials) can be flowed into the internal space, including, without limitation, any of the antimicrobials set forth above. In some embodiments, however, a solution comprising iodine, water, alcohol, and/or any other solute is flowed into the internal space. Indeed, in some embodiments, the solution comprises a copper-iodine-complex solution (e.g., as produced by Clyra Medical Technologies Inc. of Westminster, Calif., USA). In some such embodiments, such a solution can be relatively safe to use, can be highly effective at killing and otherwise reducing biofilms and other contaminants, can be non-cytotoxic, and/or can otherwise help reduce contaminants in a patient and/or to prevent the need for more aggressive procedures (e.g., implant replacement).

The antimicrobial can be introduced into an internal space of the patient in any suitable manner (including, without limitation, in any manner that the contaminant disrupting chemical and/or the flushing agent can be introduced into and/or be removed from the internal space, as discussed above). Indeed, in some embodiments, the antimicrobial is introduced into and/or flowed through the internal space by: being introduced into the patient through one or more openings 30; being introduced into and then left indefinitely in the internal space (e.g., to be resorbed and/or to be permanently left in the patient); being flowed into and/or through the internal space so that at least a portion of the antimicrobial has a dwell time within the internal space (or capsule) of between about 0.1 second and about 7 days, or any subrange thereof (e.g., between about 5 seconds and about 1 day, between about 10 seconds and about 2 hours, between about 5 minutes and about 45 minutes, etc.); having a hydrostatic and/or laminar flow while flowing into, through, and/or out of the internal space; having a turbulent flow while flowing into, through, and/or out of the internal space; being introduced into the internal space at a pressure between about 0 psi and about 250 psi (or within any subrange thereof), including, without limitation, between about 0.5 psi and about 10 psi; being introduced into the internal space intermittently; being continuously and/or continually flowed into and out of the internal space; by being used to inflate and deflate the internal space (e.g., either once or multiple times); being withdrawn from the internal space through suction (e.g., from a negative pressure wound therapy device, a vacuum, an aspirator, and/or any other device or technique that is capable of sucking the antimicrobial from the internal space); having pressure be applied to an external surface of the patient to force the antimicrobial to exit the internal space through one of the openings; and/or in any other suitable manner.

Indeed, in some embodiments, the antimicrobial comprises a fluid, gel, gas, powder, liquid, and/or other material that is flowed into, and is left in, the internal space. In some other embodiments, however, the antimicrobial comprises a fluid, gel, and/or other material that is flowed into and out of the internal space (e.g., via a lavage technique and/or otherwise) to help the antimicrobial contact a surface of an implant and/or internal tissue surrounding the implant and to have an antimicrobial effect on contaminants within the internal space. In some such embodiments, as the antimicrobial flows through the internal space, it has a turbulent flow that helps the antimicrobial to disrupt contaminants (e.g., biofilm) in the internal space. In some other embodiments, the antimicrobial flows into the closed portion of the patient (e.g., through one or more openings 30) and then (at least a portion of) the antimicrobial is allowed to dwell within the closed portion of the patient for between about 1 second and about 8 hours, or within any subrange thereof (e.g., for less than about 45 minutes). In some cases, even when a portion of the antimicrobial is removed from the closed portion of the patient, some amount of antimicrobial is left in the patient to provide extended antimicrobial protection to the patient (e.g., to offer longer antimicrobial protection, to reduce colonization of any foreign material left behind in the patient, and/or for any other suitable purpose).

Although some embodiments of the antimicrobial treatment set forth in box 20 of FIG. 1 simply include flowing an antimicrobial through the internal space, some other embodiments of the antimicrobial treatment process include any other suitable step or procedure that helps to reduce contaminants in the internal space. By way of non-limiting example, some embodiments of the antimicrobial treatment set forth at box 20 include applying vibrations to the antimicrobial in the internal space, heating the antimicrobial (e.g., prior to and/or while it is in the internal space), providing an electrical charge to the antimicrobial, using the antimicrobial to repeatedly inflate and/or deflate the internal space, using a camera to find contaminants (e.g., bacterial growth) and then directing the antimicrobial and/or a debriding tool (or any other suitable device for disrupting bacteria) towards the contaminants, and/or otherwise applying any of the aspects of the contaminant disruption process and/or flushing process (e.g., as described above) to the antimicrobial treatment.

With reference now to box 22, FIG. 1 shows that some embodiments of the method 10 optionally include flushing one or more fluids through one or more of the openings 30 to remove one or more: antimicrobials, contaminants, contaminant disruption chemicals, abrasive materials, rinsing agents, and/or other materials or objects in the patient. In this regard, any suitable material can be flushed through the patient to remove the antimicrobial, including, without limitation, water, a saline solution, a different antimicrobial, a contaminant disruption chemical, and/or any other suitable material or rinsing agent. Indeed, in some embodiments, after an antimicrobial is flowed through an internal space in the patient, a saline solution is optionally used to flush and rinse the antimicrobial and any loose contaminants from the internal space.

Where the internal space in a patient is rinsed and/or otherwise flushed after application of the antimicrobial, such flushing can occur in any suitable manner (including, without limitation, in any manner that the contaminant disrupting chemical, the flushing agent, and/or the antimicrobial can be introduced into and/or be removed from the internal space, as discussed above). Indeed, in some embodiments, a rinsing or flushing agent (e.g., water, saline, another antimicrobial, a disruption chemical, a gel, a gas, a fluid, and/or any other suitable fluid or other phase of material) is: flowed through one or more of the openings 30 into and/or through the internal space with a laminar and/or hydrostatic flow; flowed into and/or through the internal space with a turbulent flow; jetted into and/or through the internal space; intermittently flowed into and/or through the internal space; continuously and/or continually flowed into and/or through the internal space; allowed to dwell within the internal space for any suitable amount of time, including, without limitation, between about 0.1 second and about 24 hours, or within any subrange thereof (e.g., between about 1 second and about 60 seconds); flowed through the internal space via a pulsed lavage technique; flowed through the internal space via a lavage technique; removed from the internal space through suction (e.g., from a negative pressure wound therapy device, a vacuum, an aspirator, and/or any other suitable device or technique); and/or is otherwise flowed into and/or through the internal space. In some embodiments, the rinsing is done with an antimicrobial, such that debris, bacteria, and other contaminants are flushed from the patient, while the antimicrobial continues to provide antimicrobial effects to the patient (in some cases, even as some antimicrobial is left behind in the patient).

Although some embodiments of the flushing set forth in box 22 of FIG. 1 simply include flushing materials from the internal space, some other embodiments of the flushing process include any other suitable step or procedure that helps to remove materials and/or contaminants in the internal space. By way of non-limiting example, some embodiments of the flushing set forth at box 22 include applying vibrations to fluids in the internal space and/or fluids therein; heating flushing agents; providing electrical charges to the flushing agents; using the flushing agents to repeatedly inflate and/or deflate the internal space; mechanically, chemically, enzymatically, and/or otherwise disrupting contaminants in the internal space; using a camera and/or other sensor to identify bacteria and/or biofilm in the internal space; and/or otherwise applying any of the elements of the contaminant disruption process and/or the antimicrobial treatment (e.g., as described herein) to the flushing process.

In accordance with some embodiments, one or more of the openings 30 are maintained in the patient for a period of time after the antimicrobial has been applied to the internal space of the contaminated or potentially contaminated portion of the patient (e.g., near an implant). In some such embodiments, the antimicrobial (and/or any other suitable material) can be introduced into the internal space on more than one occasion. For instance, by leaving the openings (and/or conduits 44) in the patient, the patient can get multiple antimicrobial treatments (e.g., through out a day, over a course of days, and/or at any other suitable time). In some other embodiments, however, the entire method 10 is performed in a relatively short period of time, including, without limitation, between about 1 minute and about 10 hours, or within any subrange thereof (e.g., between about 15 minutes and about 8 hours, or between about 30 minutes and about 2 hours).

At some point in the method 10, box 24 of FIG. 1 shows that, in accordance with some embodiments, the openings 30 are optionally closed. In this regard, the openings can be closed at any suitable time, including, without limitation, directly after treatment of the internal space with an antibiotic, directly after the antibiotic is flushed from the internal space, after the internal space has been treated on multiple occasions by having an antibiotic be introduced into the internal space through one or more openings, after the internal space receives a contaminant disruption treatment, at completion of the method 10 during a single surgical procedure, and/or at any other suitable time. Indeed, in some embodiments, after the antibiotic has been flowed through the internal space (e.g., via one or more openings in a closed surface of the patient's skin), a practitioner closes the openings.

Where the openings 30 are closed, the openings can be closed in any suitable manner, including, without limitation, by being stitched, sutured, stapled, glued, adhered, clamped, bandaged, allowed to close and heal on their own, and/or by otherwise closing or allowing the openings to close. Indeed, in some embodiments, the openings are stitched shut.

The described method 10 (and all other methods describe herein) can be modified in any suitable manner. In this regard, any suitable portion of the methods can be omitted, added to, reordered, repeated, performed simultaneously with another portion, performed independently, performed partially, substituted with another technique, and/or otherwise be modified in any suitable manner that allows one or more contaminants to be reduced in a patient.

Indeed, in some embodiments, once the method 10 (or a variation thereof) is completed, the method (or a portion or variation thereof) is repeated. For instance (and as mentioned above), in some cases, a patient can receive multiple treatments with the antimicrobial flowing through one or more openings 30 into and/or out of an internal space in the patient. In this regard, such treatments can be provided back to back and/or with a period of time between such treatments.

As another example of a variation of the method 10, in some embodiments, the antimicrobial is introduced into the internal space in the patient, but it not flushed from or flowed out of the internal space through one of the openings. In another example, instead of simply being performed prior to the introduction of the antimicrobial into the internal space, contaminants in the internal space are disrupted (e.g., via ultrasound, sonic vibrations, an ultrasonic brush, a low frequency ultrasonic transducer disposed within a saline and/or any other suitable solution within the closed portion of the patient, application of an abrasive material, mechanically, application of a pressurized fluid, and/or in any other suitable manner) before, during, and/or after the antimicrobial is introduced into the internal space through the openings. In some embodiments, the contaminant disruption chemical is free from an antimicrobial. In other embodiments, however, the contaminant disruption chemical comprises one or more antibiotics. In yet other embodiments, the method omits any contaminant disruption outside of the application of the antimicrobial to the internal space. In still other embodiments, however, the method includes effectuating any suitable combination of contaminant disruption contaminants (or potential contaminants) within an internal space in a patient.

As another example of a variation of the described method 10, in some embodiments, when the antimicrobial (and/or any other suitable fluid) is introduced into the internal space, such fluid is caused to flow more rapidly into the internal space than it flows out. As a result of this differential flow, in some cases, the antimicrobial (and/or other fluid) causes that portion of the patient to expand and/or to otherwise inflate with the antimicrobial (and/or other fluid). As the antimicrobial (or other fluid) is able to flow through the inflated portion of the patient, the antimicrobial is able to spread throughout, expand, leak into, permeate, and penetrate into various portions of that portion of the patient so as to help ensure that the antimicrobial contacts and reacts with contaminants that may otherwise not be readily accessible to the antimicrobial. Additionally, in some cases, this differential flow causes the antimicrobial (or other fluid) to churn, swirl, and/or to otherwise mix (e.g., with contaminants) within such internal space. Accordingly, in some cases, this differential flow helps to churn up contaminants and to ensure that they are exposed to the antimicrobial.

Where the antimicrobial and/or other fluid flows into the portion of the patient that comprises an implant faster than such fluid flows out, the flow differential can be created in any suitable manner. Indeed, in some cases, the portion of the patient being treated comprises: fewer outlets than inlets, one or more inlets having a larger inner diameter than does the fluid outlet(s), one or more fluid outlets (e.g., outlet conduits) that are valved (e.g., with a variable valve and/or other suitable valve) to control fluid outflow; one or more inlets that are valved so as to provide for increased inflow; and/or any other suitable feature that allows fluid to flow into that portion of the patient faster than it exits (at least for some portion of the time that such fluid is flowed into that portion of the patient).

In some cases, once the portion of the patient has been inflated (e.g., with the antimicrobial and/or any other suitable fluid), the rate of inflow to and outflow from that portion of the patient are maintained at similar levels so as to continue to flush (while maintaining inflation of) that portion of the patient. In this regard, such inflow and/or outflow rates can be modified in any suitable manner that allows the method function as just described. For instance, one or more valves, pumps, flow limiters, actuators, vacuums, and/or other aspects of the described systems and methods can be slowed, sped up, stopped, started, and/or otherwise be modified (e.g., automatically and/or manually) to obtain a flow equilibrium that keeps the portion of the patient inflated for a desired period of time.

To help the antimicrobial (and/or any other suitable fluid) penetrate and spread throughout a portion of a patient that comprises an implant, in some cases, once the antimicrobial and/or other fluid is introduced into that portion of the patient, that portion of the patient is moved through a range of motion, bent, worked, massaged, rubbed, vibrated (e.g., with a vibrating mechanism that is disposed outside and/or inside the internal space), and/or otherwise manipulated. Indeed, in some cases in which the portion of the patient that is being treated is a joint (e.g., a knee, hip, etc.), that joint is moved through a range of motion to help the antimicrobial to flow throughout the joint to help reduce contaminants that would likely have received little to no (or at least not a desired amount of) exposure to the antimicrobial without such manipulation.

As another example of a suitable modification of the described method 10, in some embodiments, one or more biocompatible contaminant dyes and/or other markers (e.g., ruthenium red, alcian blue, gram stain, acid-fast stain, India ink, nigrosine, malachite green, safanin, methylene blue, crystal violet, fuchsin, carbolfuchsin, eosin, acid fuchsin, rose Bengal, Congo red, and/or any other suitable dye; one or more electrical charge devices and/or sensors that are configured to mark and/or detect biofilm and/or bacterial growth so as to distinguish them from healthy tissues; biofilm and bacteria staining devices; and/or other suitable markers and contaminant marking devices that are capable of dying and/or otherwise marking contaminants, such as biofilm, within the patient) are introduced into the internal space of the patient (and/or otherwise used) through one or more of the openings 30 in the closed surface of the patient's skin. In some such embodiments, a camera (e.g., as mentioned above) and/or another suitable sensor is inserted into one of the openings to allow a practitioner to see and/or to otherwise identify and/or quantify contaminants within the patient. In some embodiments, once the practitioner locates the contaminants, the practitioner is able to disrupt and/or otherwise treat such contaminants (e.g., as discussed above). In this regard, once a practitioner identifies contaminants (e.g., with or without identification of a dye or marker within an internal space), the contaminants can be disrupted and/or otherwise treated in any suitable manner, including, without limitation, through ultrasound (and/or any other suitable form of sonic energy), by being mechanically contacted and disrupted (e.g., with a brush, a deburring tool, a debriding tool, a scouring pad, by directing a fluid to such contaminants, and/or in any other suitable manner), by having an electrical field be applied to such contaminants, by having one or more contaminant disruption chemicals be applied to the contaminants, by having an abrasive material be applied to such contaminants, and/or by otherwise disrupting or treating such contaminants. In such a manner, the described systems and methods can help a practitioner to effectively: apply an antimicrobial to contaminants, remove such contaminants through suction, and/or otherwise treat such contaminants.

By way of non-limiting example, in some embodiments, an arthroscopic camera that is capable of detecting bacteria (e.g., bacteria that is not visible with the naked human eye) is inserted into an internal space of a patient through a first opening, an inlet (e.g., for inflow of the antimicrobial and/or other fluids) is provided through a second opening, a contaminant disruption tool (e.g., a brush, a deburring tool, a debriding tool, a scouring pad, and/or any other suitable tool) is inserted into the internal space through a third opening, and an outlet (e.g., coupled to a suction device, drain, or any other suitable receptacle) is provided through a fourth opening. In some such embodiments, a practitioner can easily identify, disrupt, and remove contaminants from the internal space.

As another example of a suitable modification, some embodiments of the described method 10 include measuring an amount and/or any other characteristic of biomass and/or other material that is removed from the patient through the opening 30 or openings formed in the patient. Thus, in some such embodiments, such information can help a practitioner know: how extensive the contamination was, how long to continue the treatment (e.g., based on how much biomass or contamination is exiting the patient), if the contamination has been eradicated, how effective the treatment has been, and/or any other suitable information that can be gathered by measuring and/or otherwise characterizing biomass and/or other materials that exit the internal space through one or more of the openings.

The amount and/or any other characteristic of biomass and/or other materials that are removed from the patient can be measured in any suitable manner, including, without limitation, via one or more flow cytometers, hemocytometers, image-based cell counters, automated cell counters, fluorescent cell counters, Coulter counters, spectrophotometry devices, impedance counting devices, centrifuge techniques, and/or in any other suitable manner. Indeed, in some embodiments, one or more sensors are used to determine the opacity and/or color of fluids that flow out of the internal space so as to determine how extensive the contamination is and/or the effectiveness of the method.

As another example of a modification, in some embodiments, a sample of fluid released from the internal space (e.g., as the space is flushed after contaminant disruption and/or antimicrobial treatment) is spread on a petri dish (or otherwise added to a culture medium) to check for bacterial growth and to determine the effectiveness of the treatment.

As even an additional example of a suitable modification, some embodiments of the described system and methods involve disrupting contaminants in and/or applying one or more antimicrobials into an orifice, tissue, organ, and/or other closed portion of a body. Indeed, in some embodiments, the described systems and methods (or variations thereof) are configured to disrupt contaminants, to apply an antimicrobial to contaminants, and/or to otherwise reduce contaminants in a patient's larynx, trachea, bronchi, tear duct, nostril, nose, nasal cavity, anus, colon, esophagus, mouth, urethra, bladder, kidney, ureter, artery, vein, and/or in any other orifice in a closed portion of the patient.

In this regard, the described systems and methods can be modified in any suitable manner that allows them to function as described. In some embodiments, a tube and/or other conduit is inserted into a larynx, trachea, anus, urethra, tear duct, ear canal, primary brachia, secondary brachia, mouth, and/or other natural orifice in the patient. In some such embodiments, a liquid, gas, mist, and/or other carrier comprising one or more contaminant disruption chemicals and/ or antimicrobials is then introduced into the orifice through an end, side, top, bottom, middle, and/or other portion of the conduit. Indeed, in some embodiments, one or more walls and/or other portions of the conduit are porous, permeable, comprise one or more holes that extend therethrough, and/or are otherwise configured to allow a medium (e.g., a mist (such as a vapor, steam, atomized material, nebulized material, and/or any other suitable mist), drips of material, streams of materials, and/or any other suitable form of material) comprising one or more antimicrobials and/or disruption chemicals to pass through the walls. For instance, in some cases in which such a conduit is intubated in a patient's trachea, mist, water droplets, and/or another medium comprising an antimicrobial and/or disruption chemical coats an outer surface of the conduit to help break up, disrupt, kill, and otherwise reduce contaminants that are on or around the conduit.

In some embodiments in which one or more conduits are used to supply one or more antimicrobials and/or disruption chemicals into an orifice in a patient's body (e.g., trachea, tear duct, etc.), one or more additional conduits are optionally used to suck, aspirate, draw, absorb, and/or otherwise remove the antimicrobials, disruption chemicals, contaminants, and/or other materials from the body (e.g., orifice). Indeed, in some embodiments, a first conduit that delivers antibiotics and/or disruption chemicals is in proximity to (e.g., side by side with, disposed within, disposed over, and/or is otherwise close to) a second conduit that is coupled to a negative pressure wound therapy device, a vacuum, an aspirator, and/or any other suitable device that is capable of drawing, wicking, sucking, and/or otherwise removing materials from the orifice. As a result, some such embodiments can prevent antimicrobials, disruption chemicals, and/or contaminants from pooling in the orifice or elsewhere.

Thus, some embodiments of the described systems and methods relate to a method for applying and/or extracting a fluid from a closed portion of a body by placing a conduit in the closed portion of the body (e.g., via a larynx, mouth nostril, and/or other suitable orifice); and flowing an antimicrobial solution through the conduit into the closed portion of the body such that the antimicrobial solution contacts an internal surface in the closed portion of the body, wherein the antimicrobial solution comprises an antimicrobial mist (i.e., a nebulized antimicrobial solution and a vaporized antimicrobial solution), and wherein the flowing the antimicrobial solution through the conduit into the closed portion of the body comprises contacting the antimicrobial solution with an outer surface of the conduit.

As still another example of a suitable modification, some embodiments of the described method 10 are used to clean an infected or otherwise contaminated joint (or other portion of the patient) that does not have an implant. In still another example, some embodiments of the described systems and methods are used in one or more wound beds, organs, tissues, and/or other locations of a patient that have or do not have an implant and that are covered with skin that is substantially closed but for the openings 30.

In addition to the aforementioned features, the described methods 10 can have any other suitable feature. Indeed, unlike some conventional techniques that require an implant to be substantially exposed in order to allow infection around the implant to be effectively treated, some embodiments of the described systems and methods are configured to keep a patient's skin substantially closed and the implant substantially (if not completely) covered with skin while contamination in the patient is treated through one or more relatively small openings 30 in the skin. Accordingly, some embodiments of the current invention: are relatively non-invasive, involve a lower likelihood of introducing new contaminants into the patient, are relatively easy to recover from, are relatively less painful, are relatively less expensive, have a lower likelihood of requiring bone and/or significant tissue removal, are less traumatic, are more reproducible with less patient impact, are relatively simple to perform, are relatively faster to perform, involve less anatomical destruction of a patient's body, are relatively less traumatic, and/or are otherwise more desirable than are some conventional methods.

Moreover, unlike some conventional systems and methods that take significant periods of time to treat infection near an implant, some embodiments of the described method 10 are configured to be completed (e.g., from forming the openings 30 at box 14 of FIG. 1 to closing the openings at box 24 (and completing any desired portions of the method therebetween) in less than about 8 hours (e.g., in less than about 2.5 hours).

Additionally, unlike some conventional techniques for treating infections near an implant that require removal of the implant, some embodiments of the described systems and methods are configured to effectively treat infection around an implant without having the implant be removed and/or replaced. Again, some such embodiments can effectively treat infection around an implant, while sparing the patient from other aggressive, painful, costly, dangerous, and otherwise undesirable conventional techniques.

As still another example of a feature, some embodiments of the described systems and methods are configured to have one or more antimicrobials diffuse, melt, vibrate into, be sprayed into, soak into, leach into, and/or otherwise penetrate between a surface of an implant and an adjacent portion of a bone. In some such embodiments, the described systems and methods can be used to treat infections in bone that is covered with an implant without removing the implant. In this regard, the antimicrobial can penetrate in between the bone and the implant in any suitable manner, including, without limitation, by being vibrated into such a location through sonication or ultra-sonication (e.g., by placing an ultrasonic head 80 through one of the openings 30 and near the interface between the bone and implant), by using an electrical field to drive the antimicrobial into biofilm and/or the interface between tissue and the implant, by drilling and/or otherwise forming holes in the bone (e.g., through the openings 30) near an interface between the bone so as to allow the antimicrobial to diffuse into such holes and throughout a portion of the bone, by flowing the antimicrobial into the closed portion of the patient under pressure, by allowing gravity to cause the antimicrobial to flow into the interface (and/or elsewhere), and/or in any other suitable manner. Indeed, in some embodiments, the antimicrobial is able to penetrate into the interface between a bone and an implant through a pressurized flushing technique.

As still another feature, some conventional techniques may drive non-antimicrobial fluids into a closed portion of a body. In some cases, by so doing, such techniques can actually cause contaminants to spread further within that body. In contrast, some embodiments of the described method 10 comprise forming one or more openings in a portion of a patient and then flowing an antimicrobial into that portion of the patient without first flowing a non-antimicrobial into that portion of the patient. In some such embodiments, as the antimicrobial flows into that portion of the patient and that portion of the patient expands, the antimicrobial is able to flow with the contaminants, ensuring that the contaminants are not spread throughout that portion of the patient without also being contacted by the antimicrobial.

As yet another feature, while some conventional systems and methods for treating infections around implants may be relatively ineffective at treating pathogens (e.g., the ESKAPE pathogens, such as *Enterococcus faecium, Staphylococcus aureus, Klebsiella pneumonia, Acinetobacter baumannii, Pseudomonas aeruginosa*, and/or *Enterobacter* species), some embodiments of the current systems and methods can be very effective in reducing and otherwise treating such contaminants. Indeed, in some cases, the use of one or more copper-iodine-complex solutions, such as those as produced by Clyra Medical Technologies Inc. of Westminster, Calif., USA, can be very effective at treating such contaminants through the relatively non-invasive systems and methods described herein.

As still another feature of the described systems and methods, some embodiments of such systems and methods are relatively non-invasive (as described). As such, some embodiments of the described systems and methods can reduce time, costs, risk, and pain involved with the hospital stays, operating rooms, rehabilitation, and other effects of some conventional systems and methods for treating infections that are near an implant. Indeed, in some instances, the described systems and methods reduce recovery time and speed up the time when the patient can return to activity, work, and/or other normal activities.

Systems for Reducing Contaminants

The described method 10 can be effectuated through the use of any suitable system or apparatus that is configured to perform the functions described herein. Indeed, in some embodiments, one or more chemicals are introduced into the openings 30 in a closed portion of the patient's skin through one or more tubes, lumen, catheters, needles, and/or other conduits 44. In this regard, such conduits can further be coupled to any other item that allows them to function as intended. For instance, some embodiments of the conduits that provide fluids, gels, and/or other materials (e.g., materials comprising an antimicrobial and/or disruption chemical) into the internal space through the openings are coupled to one or more syringes, bags, containers, bottles, suction and/or pressure pumps, recipients, and/or other apparatus that are configured to hold and/or feed such fluids, gels, and/or other materials into the internal space. Additionally, some embodiments of the conduits that receive fluids, gels, and/or other materials that exit the internal space through the openings are coupled to one or more syringes, bags, containers, bottles, suction and/or pressure pumps, recipients, and/or other apparatus that are configured to, draw, hold, and/or receive such fluids, gels, and/or other materials after (and/or as) they exit the internal space.

The materials that are moved into and/or out of the internal space through the openings 30 (e.g., the antimicrobial, the disruption chemical, etc.) can be forced into and/or out of the internal space in any suitable manner, including, without limitation, by being forced by gravity (e.g., by being raised above a portion of the patient and being allowed to be gravity fed into and/or being lowered below a portion of the patient and being allowed to flow out of patient by gravity); by being forced by one or more pumps, aspirators, negative pressure therapy devices, positive pressure therapy devices, syringes, tubing, lavage devices, pulsed lavage devices, static lavage devices; and/or in any other suitable manner. Indeed, in some embodiments, one or more pumps, lavage devices, and/or negative pressure therapy devices are used to force fluids into and/or to draw them from the internal space of the patient, through one or more of the openings.

In accordance with some embodiments, the described systems and methods include a system that is configured to both provide one or more antimicrobials (and/or any other suitable materials) into a patient and to receive such antimicrobials (and/or any other suitable materials) as they exit the patient. In such embodiments, the system can comprise any suitable component, including, without limitation, one or more: containers to hold one or more antimicrobials, disruption chemicals, and/or other materials before they are introduced into a patient through one or more of the openings; containers to hold one or more antimicrobials, disruption chemicals, contaminants, and/or other materials after they exit the patient through one or more of the openings; pumping mechanism (e.g., a pump, vacuum, aspirator, negative pressure therapy device, and/or other mechanism that is configured to move the materials into and/or out of the patient through the openings); one or more sensors (e.g., cameras, flow rate sensors, opacity censors, cell counters, thermometers, pressure sensors, dye sensors, contaminant sensors, and/or any other suitable sensors), dyes, stains, contaminant markers, guiding optics, electrolysis probes, heaters (e.g., to warm or otherwise heat fluids before they enter, and/or while they are within, the patient), valves, power sources (e.g., batteries, plugs, and/or other mechanisms for powering the device), timers (e.g., to track how long a treatment is taking, to determine when a portion of a treatment should take place, and/or for any other suitable purpose), processors (e.g., to control the system based one or more programs and/or user input); to determine an amount, dilution, pressure, temperature, concentration, and/or other characteristic of materials being supplied into the internal space in the patient; to control the pumping mechanism and/or any other suitable portion of the system); and/or any other suitable portion of the system.

Figure 4:
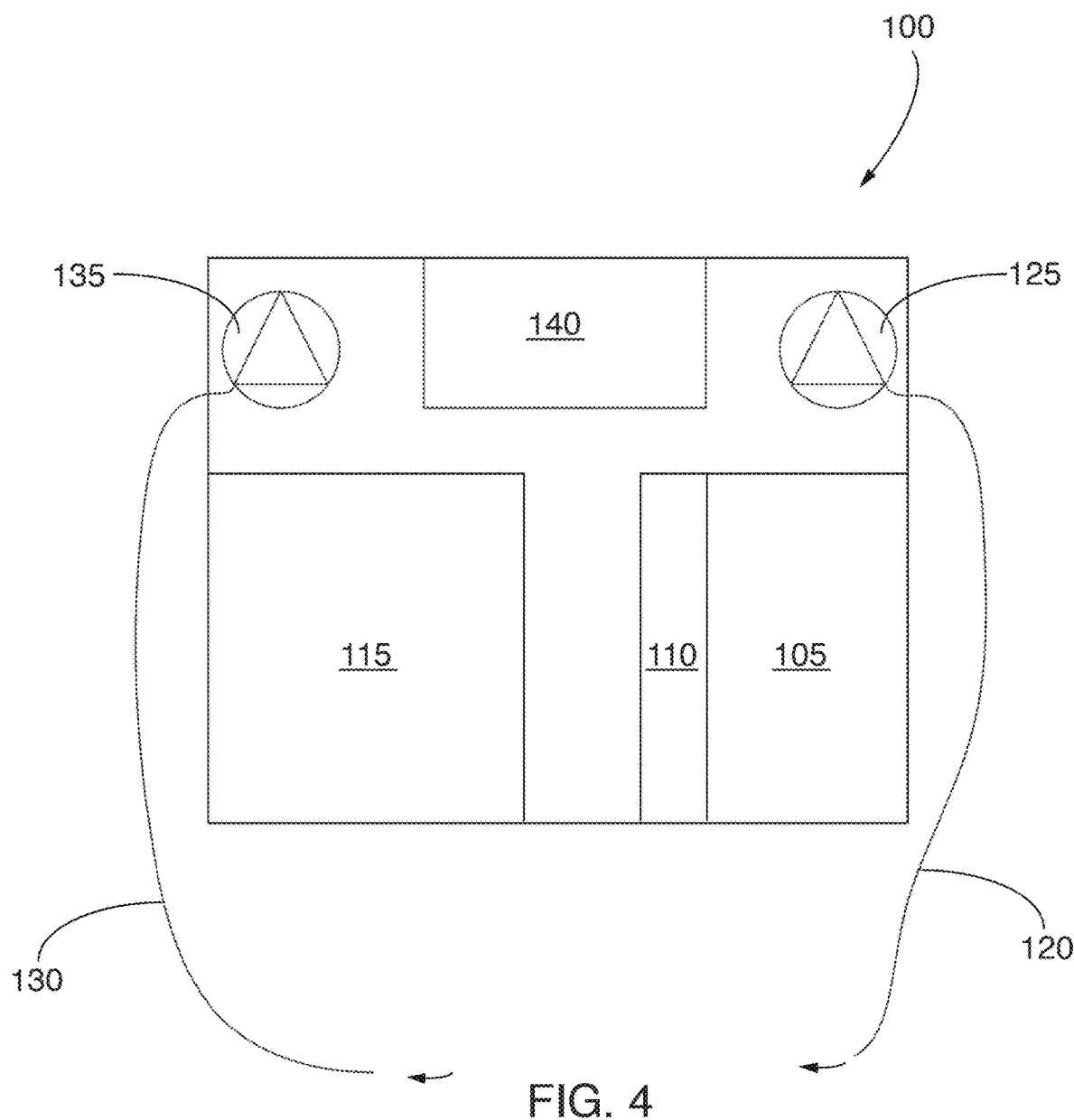
FIG. 4 illustrates a system for reducing contaminants in a patient in accordance with a representative embodiment.

By way of non-limiting illustration, FIG. 4 shows that in accordance with some embodiments, a system 100 for reducing contaminants in a portion of a patient comprises: a first container 105 and a second container 110 for holding one or more materials (e.g., disruption chemicals, antimicrobials, rinsing agents, etc.) that are to be introduced into a patient through one or more openings; a third container 115 for receiving materials (e.g., used antimicrobial, used disruption chemicals, contaminants, etc.) that exit the patient through one or more openings; a first conduit 120 and first pump mechanism 125 that are configured to feed materials into the patient; a second conduit 130 and second pump mechanism 135 (e.g., a suction pump and/or any other suitable pump) that are configured to draw materials from the patient; and a processor 140.

Thus, in some embodiments, the described system 100 is automated, portable, configured for extended use, capable of being operated by patients and/or practitioners, and/or otherwise provides a relatively convenient mechanism for providing the described method 10 to a patient. Indeed, in some cases, such a system is configured to be used by a patient (e.g., at home, in a care facility, and/or outside of a care facility).

Additionally, in some such embodiments in which the system 100 comprises a processor, the processor can perform any suitable function. Indeed, in some such embodiments, the processor is configured to: run one or more programs; receive and execute commands provided by a practitioner; determine when a particular fluid is to flow from and/or into the system; determine a rate and/or pressure at which one or more fluids flow from and/or into the system; control a dwell time of fluid in the internal space of the patient; control a temperature of fluid in and/or flowing from the system (e.g., via a heater in the system or otherwise); control an arthroscopic camera that is in signal communication with the system; control an ultrasonic head 80 and/or other tool that is in communication with the system; gather, store, and/or analyze information regarding system usage; store and/or modify operating parameters; and/or perform any other suitable function. Additionally, in some embodiments, the processor allows the described system to provide information it gathers (and/or to otherwise be controlled) remotely.

Implants for Reducing Contaminants

In accordance with some embodiments, the described systems and methods relate to one or more implants and/or washes (e.g., as described above) that comprise one or more antimicrobials. Accordingly, in some cases, one or more such implants and/or washes can be implanted and/or otherwise introduced into a patient, and thereby help the patient to avoid and/or reduce infection and/or other forms of contamination from developing near such implant.

With respect to the washes, in some embodiments (as discussed above), one or more antimicrobials (e.g., antimicrobial gels, fluids, and/or other antimicrobial substances) are optionally not rinsed, from, not completely rinsed from, and/or are not otherwise completely removed from the closed portion of the patient. Indeed, as discussed above with respect to the method 10 of FIG. 1, in some embodiments, the method does not include a rinse or flush of the antimicrobial from the internal space following treatment with the antimicrobial under box 20 of FIG. 1 such that at least some antimicrobial is left in the internal space.

Where some antimicrobial is left in an internal space of the patient, such antimicrobial can be retained in the patient in any suitable manner. Indeed, in some embodiments, one or more openings 30 in the patient are closed (e.g., capped, valved closed, stitched shut, bandaged, stapled, glued, and/or otherwise closed) while some amount of an antimicrobial substance (e.g., gel, powder, fluid, etc.) is left within the closed portion of the patient. In this regard, such material can be configured to be resorbed into the patient, to be left in the patient for an extended period of time and then to be removed, and/or to be permanently left in the patient.

In some embodiments, materials (e.g., one or more antimicrobials) are left in the patient for a desired period of time and are then rinsed from the patient at a later date (e.g., one or more of openings are reformed, newly formed, valved open, unplugged, unstopped, and/or otherwise opened such that some or all of the antimicrobial can be rinsed from the joint, cavity, dead space, organ, wound bed, and/or other closed portion of the patient). In some other embodiments, however, such materials are left in the patient permanently or (in some cases) until they are resorbed.

With respect to the implants, the described systems and methods can (where an implant is used) use any suitable implant, including, without limitation, one or more permanent implants, resorbable implants, orthopedic implants, cosmetic implants, and/or any other suitable implants (e.g., as set forth above). Indeed, in some embodiments, the implant comprises an orthopedic implant, a pin, a bead, a piece of film, a screw, a bolt, a mesh, a structural support, cosmetic implant, and/or any other suitable implant that is coated with, impregnated with, and/or that otherwise comprises one or more antimicrobials.

With respect to the antimicrobial, the implant can comprise any suitable antimicrobial or combination of antimicrobials, including, without limitation, one or more metals, antibiotics, antifungals, biocides, enzymes, and/or other suitable antimicrobials (e.g., as set forth above). Indeed, in some embodiments, the antimicrobial comprises silver; gold; copper; iodine; zinc; HOCl; PHMB, one or more heavy, biocompatible metals; one or more dilute iodine solutions; one or more copper-iodine-complex solutions (e.g., wherein the free iodine in such solution remains below its solubility factor to provide a non-cytotoxic but efficacious antimicrobial); one or more cationic metals; one or more anionic metals; one or more alloys or derivatives of any of the foregoing; and/or any other suitable material having antimicrobial characteristics The antimicrobial can be applied to the implant in any suitable manner that allows it to be used as described herein. Indeed, in some embodiments, one or more antimicrobials (and/or other materials, such as an anti-inflammatory) are: coated on, anodized on, vapor deposited on, layered on, infused into, impregnated in, disposed in a reservoir within, disposed within a balloon of, associated with delayed release polymers of, associated with resorption polymers of, formed with, associated with a delayed delivery mechanism of, and/or otherwise placed on, within, and/or adjacent to the implant. In some cases, however, silver, gold, iodine, zinc, and/or another antimicrobial material is anodized onto a surface of the implant.

In some other embodiments, however, the antimicrobial is (as mentioned above) impregnated into, disposed in a reservoir within, and/or otherwise configured to be released slowly (or over an extended period of time) from the implant. Indeed, some embodiments of the described implants comprise one or more materials that are configured to slowly release an antimicrobial. Some examples of such a material include, without limitation, PMMA, calcium phosphate, calcium sulfate, glass, collagen, gelatin, hydrofibers, carrageenan, silver, gold, copper, HOCl, iodine, PHMB, and/or any other lattice, matrix, and/or other material that is suitable for use in a patient and that is configured to release the antimicrobial over time.

Although some embodiments of the described implants are configured to be disposed in a patient for the duration of the patient's life, in some other embodiments, the implant comprising one or more antimicrobials comprises one or more resorbable materials that are configured to be resorbed into the patient. Some examples of such materials include, but are not limited to, calcium sulfate, calcium phosphate, collagen, carrageenan, gelatin, hydrofiber, resorbable glass, and/or any other suitable material that can comprise an antimicrobial and be resorbed into the patient. Indeed, in some embodiments, one or more beads, gels, films, meshes, and/or other suitable implants that comprise one or more antimicrobials further comprise a material that is configured to be resorbed into the patient. Accordingly, in some cases, a resorbable implant (e.g., one or more beads, pins, plates, gels, powders, and/or other suitable implants) with one or more antimicrobials can be implanted into a person, where the implant can act as antimicrobial device for an extended period of time (e.g., until it is resorbed).

Representative Operating Environment

The described systems (e.g., system 100) and methods (e.g., method 10) can be used with or in any suitable operating environment and/or software. In this regard, FIG. 6 and the corresponding discussion are intended to provide a general description of a suitable operating environment for a system for reducing contamination in a patient in accordance with some embodiments of the described systems and methods. As will be further discussed below, some embodiments embrace the use of one or more processing (including, without limitation, micro-processing) units (e.g., processors 140, as discussed above)) in a variety of customizable enterprise configurations, including in a networked configuration, which may also include any suitable cloud-based service, such as a platform as a service or software as a service.

Some embodiments of the described systems and methods embrace one or more computer readable media, wherein each medium may be configured to include or includes thereon data or computer executable instructions for manipulating data. The computer executable instructions include data structures, objects, programs, routines, or other program modules that may be accessed by one or more processors, such as one associated with a general-purpose processing unit capable of performing various different functions or one associated with a special-purpose processing unit capable of performing a limited number of functions. In this regard, in some embodiments, the processing unit 140 (e.g., as mentioned above) comprises a specialized processing unit that is configured for use with the described system 100 and methods 10.

Computer executable instructions cause the one or more processors of the enterprise to perform a particular function or group of functions and are examples of program code means for implementing steps for methods of processing. Furthermore, a particular sequence of the executable instructions provides an example of corresponding acts that may be used to implement such steps.

Examples of computer readable media (including non-transitory computer readable media) include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing unit.

Figure 6:
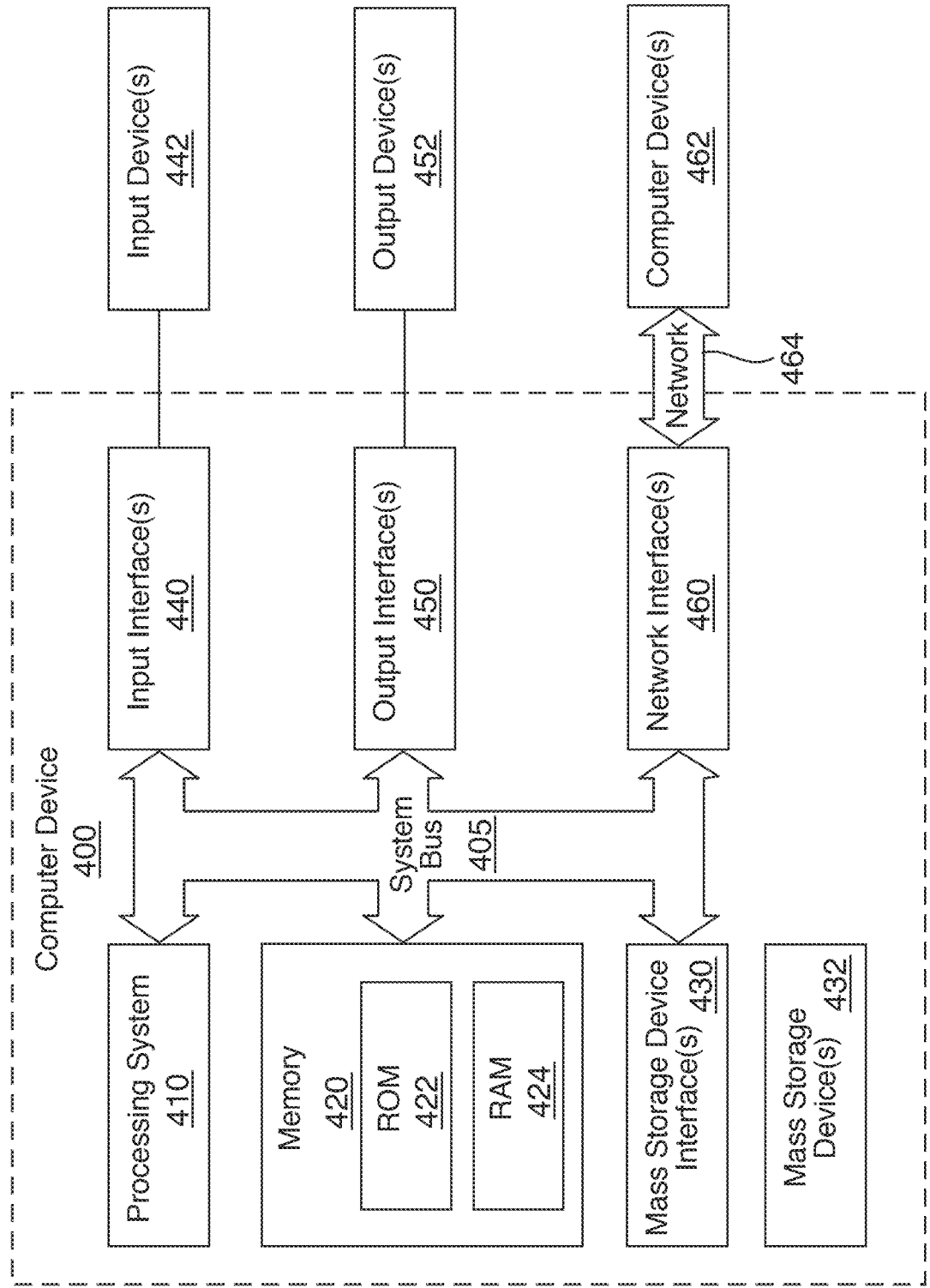
FIG. 6 illustrates a representative system that provides a suitable operating environment for use with some embodiments of the described system.

With reference to FIG. 6, a representative system includes a computer device 400 (e.g., processor 140 or other unit), which may be a general-purpose or special-purpose computer (or processing unit). For example, computer device 400 may be a personal computer, a notebook computer, a PDA or other hand-held device, a workstation, a system for reducing contaminants in a patient 100 (e.g., as described above), a minicomputer, a mainframe, a supercomputer, a multi-processor system, a network computer, a processor-based consumer device, a cellular phone, a tablet computer, a smart phone, a feature phone, a smart appliance or device, a control system, or the like.

In accordance with some embodiments, computer device 400 includes system bus 405, which may be configured to connect various components thereof and enables data to be exchanged between two or more components. System bus 405 may include one of a variety of bus structures including a memory bus or memory controller, a peripheral bus, or a local bus that uses any of a variety of bus architectures. Typical components connected by system bus 405 include processing system 410 and memory 420. Other components may include one or more mass storage device interfaces 430, input interfaces 440, output interfaces 450, and/or network interfaces 460, each of which will be discussed below.

Processing system 410 includes one or more processors, such as a central processor and optionally one or more other processors designed to perform a particular function or task. It is typically processing system 410 that executes the instructions provided on computer readable media, such as on the memory 420, a magnetic hard disk, a removable magnetic disk, a magnetic cassette, an optical disk, or from a communication connection, which may also be viewed as a computer readable medium.

Memory 420 includes one or more computer readable media (including, without limitation, non-transitory computer readable media) that may be configured to include or includes thereon data or instructions for manipulating data, and may be accessed by processing system 410 through system bus 405. Memory 420 may include, for example, ROM 422, used to permanently store information, and/or RAM 424, used to temporarily store information. ROM 422 may include a basic input/output system ("BIOS") having one or more routines that are used to establish communication, such as during start-up of computer device 400. RAM 424 may include one or more program modules, such as one or more operating systems, application programs, and/or program data.

One or more mass storage device interfaces 430 may be used to connect one or more mass storage devices 432 to the system bus 405. The mass storage devices 432 may be incorporated into or may be peripheral to the computer device 400 and allow the computer device 400 to retain large amounts of data. Optionally, one or more of the mass storage devices 432 may be removable from computer device 400. Examples of mass storage devices include hard disk drives, magnetic disk drives, tape drives, solid state mass storage, and optical disk drives.

Examples of solid state mass storage include flash cards and memory sticks. A mass storage device 432 may read from and/or write to a magnetic hard disk, a removable magnetic disk, a magnetic cassette, an optical disk, or another computer readable medium. Mass storage devices 432 and their corresponding computer readable media provide nonvolatile storage of data and/or executable instructions that may include one or more program modules, such as an operating system, one or more application programs, other program modules, or program data. Such executable instructions are examples of program code means for implementing steps for methods disclosed herein.

One or more input interfaces 440 may be employed to enable a user to enter data (e.g., initial information) and/or instructions to computer device 400 through one or more corresponding input devices 442. Examples of such input devices include a keyboard and/or alternate input devices, such as a digital camera, a sensor (e.g., a pressure sensor, cell counter, opacity sensor, pressure sensor, thermometer, and/or any other suitable sensor), bar code scanner, signature and/or writing capture device, pin pad, touch screen, mouse, trackball, light pen, stylus, or other pointing device, a microphone, a joystick, a game pad, a scanner, a camcorder, and/or other input devices. Similarly, examples of input interfaces 440 that may be used to connect the input devices 442 to the system bus 405 include a serial port, a parallel port, a game port, a universal serial bus ("USB"), a firewire (IEEE 1394), a wireless receiver, a video adapter, an audio adapter, a parallel port, a wireless transmitter, or another interface.

One or more output interfaces 450 may be employed to connect one or more corresponding output devices 452 to system bus 405. Examples of output devices include a monitor or display screen, a speaker, a wireless transmitter, a printer, and the like. A particular output device 452 may be integrated with or peripheral to computer device 400. Examples of output interfaces include a video adapter, an audio adapter, a parallel port, and the like.

One or more network interfaces 460 enable computer device 400 to exchange information with one or more local or remote computer devices, illustrated as computer devices 462, via a network 464 that may include one or more hardwired and/or wireless links. Examples of the network interfaces include a network adapter for connection to a local area network ("LAN") or a modem, BLUETOOTH™, WiFi, a cellular connection, a wireless link, or another adapter for connection to a wide area network ("WAN"), such as the Internet. The network interface 460 may be incorporated with or be peripheral to computer device 400.

Figure 7:
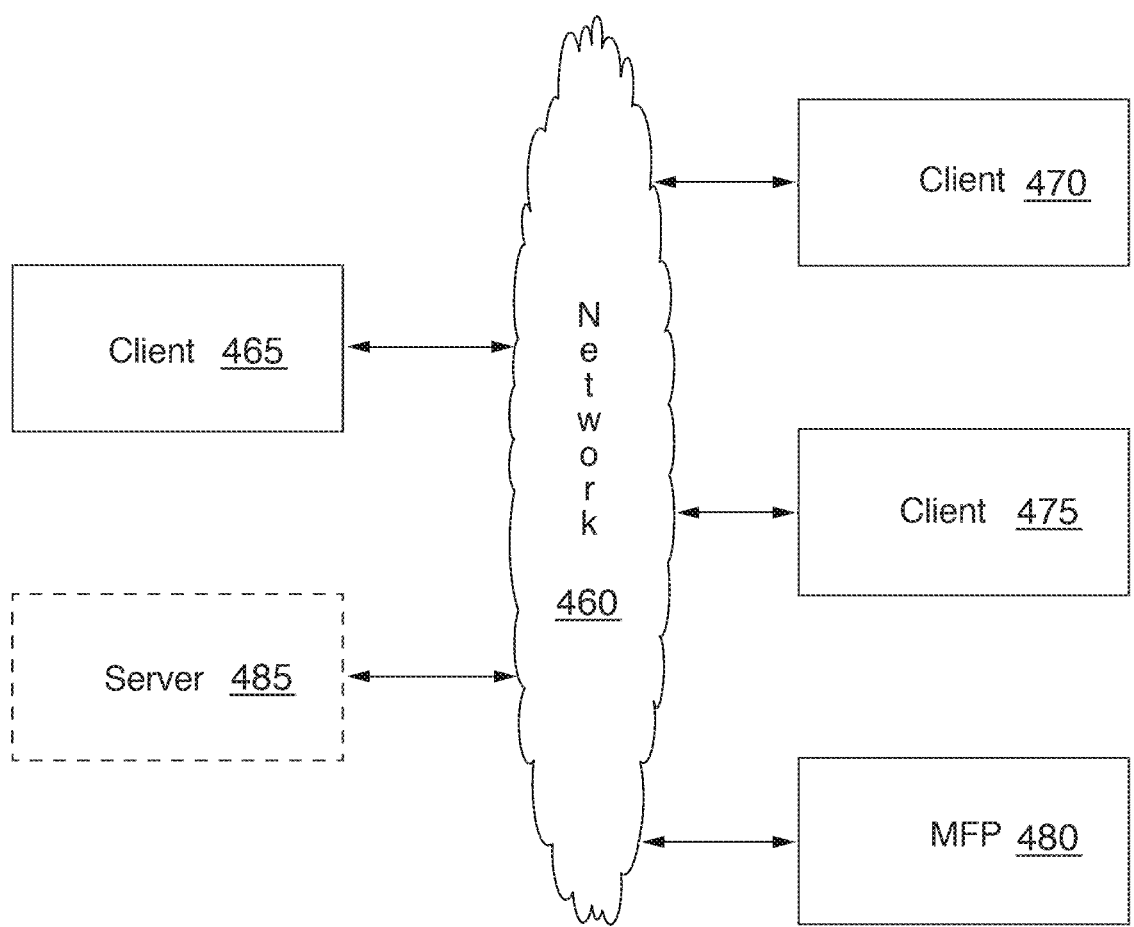
FIG. 7 illustrates a representative embodiment of a networked system that provides a suitable operating environ-

In a networked system, accessible program modules or portions thereof may be stored in a remote memory storage device. Furthermore, in a networked system computer device 400 may participate in a distributed computing environment, where functions or tasks are performed by a plurality networked computer devices. While those skilled in the art will appreciate that the described systems and methods may be practiced in networked computing environments with many types of computer system configurations, FIG. 7 represents an embodiment of a portion of the described systems in a networked environment that includes clients (465, 470, 475, etc.) connected to a server 485 via a network 460. While FIG. 7 illustrates an embodiment that includes 3 clients (e.g., systems 100, etc.) connected to the network, alternative embodiments include at least one client connected to a network or many clients connected to a network. Moreover, embodiments in accordance with the described systems and methods also include a multitude of clients throughout the world connected to a network, where the network is a wide area network, such as the Internet. Accordingly, in some embodiments, the described systems and methods can allow for remote: monitoring, training, communication, observation, control, adjustment, trouble shooting, data collecting, system optimization, user interaction, and/or other controlling of the described system 100 for reducing contaminants in a patient from one or more places throughout the world.

Thus, some embodiments of the current invention relate to systems and methods for reducing pathogens, infections, and/or other contaminants in a portion of a patient. More particularly, some embodiments of the described invention relate to systems and methods for reducing contaminants in a portion of a patient that has an implant and that is disposed interior to a closed surface of skin of the patient. The method can further include placing one or more relatively small openings into the closed surface of skin and injecting, pulsing, introducing, and/or otherwise flowing an antimicrobial material into that portion of the patient to contact the antimicrobial material with a surface of the implant and/or tissue adjacent to the implant. In some cases, the antimicrobial material flows into the portion of the patient faster than it flows out, such that differential pressure between inflow and outflow of the antimicrobial material causes that portion of the patient to inflate. In some cases, once inflated, the rate of inflow and outflow are maintained at a similar level so as to continue to flush (while maintaining inflation of) the portion of the patient. In some cases, after treatment with the antimicrobial material, it is then flushed, drained, suctioned out, or otherwise removed from the portion of the patient having the implant. As part of this method, biofilm and/or other contaminants near the implant are, in some embodiments, disrupted mechanically, ultrasonically, electrically, chemically, enzymatically, and/or in any other suitable manner. Thus, in some embodiments, the described systems and methods can treat infections and/or other contaminants near implants in a relatively non-invasive manner.

The present invention may be embodied in other specific forms without departing from its spirit or essential characteristics. The described embodiments, examples, and illustrations are to be considered in all respects only as illustrative and not restrictive. The scope of the invention is, therefore, indicated by the appended claims rather than by the foregoing description. Each of the various elements of the described embodiments, implementations, figures, and examples can be mixed and matched with each other in any suitable manner. All changes that come within the meaning and range of equivalency of the claims are to be embraced within their scope. In addition, as the terms on, disposed on, attached to, connected to, coupled to, etc. are used herein, one object (e.g., a material, element, structure, member, etc.) can be on, disposed on, attached to, connected to, or coupled to another object—regardless of whether the one object is directly on, attached, connected, or coupled to the other object, or whether there are one or more intervening objects between the one object and the other object. Also, directions (e.g., front back, on top of, below, above, top, bottom, side, up, down, under, over, upper, lower, lateral, etc.), if provided, are relative and provided solely by way of example and for ease of illustration and discussion and not by way of limitation. Where reference is made to a list of elements (e.g., elements a, b, c), such reference is intended to include any one of the listed elements by itself, any combination of less than all of the listed elements, and/or a combination of all of the listed elements. Furthermore, as used herein, the terms a, an, and one may each be interchangeable with the terms at least one and one or more.

What is claimed is:

1. A method for reducing contaminants in a portion of a patient, the portion of the patient comprising an implant that is disposed interior to a closed surface of skin of the patient, the method comprising:
    placing an inlet conduit in the closed surface of skin in the portion of the patient;
    placing an outlet conduit in the closed surface of skin in the portion of the patient;
    flowing an antimicrobial comprising a copper-iodine-complex solution:
        through the inlet conduit,
        into the portion of the patient to contact the antimicrobial with at least one of:
    (i) the implant and (ii) tissue adjacent to the implant, and out of the outlet conduit such that the antimicrobial flows into the portion of the patient faster than the antimicrobial flows out of the portion of the patient so that the antimicrobial causes the portion of the patient to inflate;
    inserting an arthroscopic camera into the portion of the patient through the inlet conduit, wherein the arthroscopic camera is configured to detect at least one of: (i) bacteria and (ii) biofilm that is not readily visible to a naked eye; and
    adding a marker to the portion of the patient to mark the at least one of the bacteria and the biofilm for detection by the arthroscopic camera.

2. The method of claim 1, further comprising using at least one of: (a) varied pressure and (b) sonic vibrations to excite the antimicrobial when the antimicrobial is within the portion of the patient and is in contact with the at least one of the implant and the tissue adjacent to the implant.

3. The method of claim 1, further comprising heating the antimicrobial at least one of:
    (i) prior to flowing the antimicrobial into the portion of the patient and (ii) while the antimicrobial is within the portion of the patient.

4. The method of claim 1, further comprising:
    removing the inlet conduit and the outlet conduit from the closed surface of skin while a portion of the antimicrobial remains in the portion of the patient; and
    closing openings through which the inlet conduit and the outlet conduit extended in the closed surface of skin.

5. The method of claim 1, wherein the antimicrobial comprises a contaminant disruption chemical selected from at least one of a base, an acid, emulsifier, surfactant, and an enzyme.

* * * * *